United States Patent [19]
Okahata

[11] Patent Number: 5,447,869
[45] Date of Patent: Sep. 5, 1995

[54] METHOD OF DETECTING BITTER OR ODOROUS SUBSTANCES AND APPARATUS THEREFOR

[75] Inventor: Yoshio Okahata, Tokyo, Japan

[73] Assignee: Sogo Pharmaceutical Company Limited, Japan

[21] Appl. No.: 75,921

[22] Filed: Jun. 14, 1993

Related U.S. Application Data

[63] Continuation of Ser. No. 666,437, Mar. 11, 1991, which is a continuation of Ser. No. 167,310, Mar. 11, 1988, abandoned.

[30] Foreign Application Priority Data

Mar. 11, 1987 [JP] Japan .................................. 62-56276

[51] Int. Cl.$^6$ ............................................ G01N 33/00
[52] U.S. Cl. .................................. 436/178; 422/68.1; 422/82.01; 422/83
[58] Field of Search ................ 422/68.1, 82.01, 82.02, 422/83, 69, 84; 436/178

[56] References Cited

U.S. PATENT DOCUMENTS

| | | |
|---|---|---|
| 4,224,595 | 9/1980 | Dolan . |
| 4,236,893 | 12/1980 | Rice ........................ 422/61 |
| 4,242,096 | 12/1980 | Oliveira et al. .............. 422/61 |
| 4,548,955 | 10/1985 | Okahata . |
| 4,735,906 | 4/1988 | Bastiaans ..................... 436/527 |
| 4,789,804 | 12/1988 | Karube et al. ................ 422/55 |

FOREIGN PATENT DOCUMENTS

| | | |
|---|---|---|
| 1294705 | 5/1969 | Germany . |
| 1673104 | 6/1972 | Germany . |

OTHER PUBLICATIONS

Hamilton et al., "A Gas Analyzer Based on the Quartz Crystal Adsorption Technique," The Institute of Physics, Bristol, GB, *Journal of Physics, E. Scientific Instruments*, vol. 19, No. 4, Apr. 1986 (received Jun. 10, 1985), pp. 271–274.

Krull et al., "Lipid Membrane Technology for Chemical and Biosensor Deveopment," *TRAC: Trends in Analytical Chemistry*, vol. 4, No. 4, Apr. 1985, Elsevier Science Publishing: Amsterdam, NL, pp. 90–96.

Kurihara, Yoshi, Kashiwayanagi, Comp. Biochem. Physiol., "Trandsuction Mechanism In Chemoreception", vol. 85A, No. 1, pp. 1–22, 1986.

Science, 54, No. 11, pp. 669–678 (1984), Kenzo Kurihara.

Science, vol. 153, Jul. 8, 1966, pp. 185–188, J. Del Castillo et al: "Lipid films as transducers for detection of antigen–antibody and enzyme–substrate reactions".

TRAC: Trends in Analytical Chemistry, vol. 4, No. 4, Apr. 1985 pp. 90–96—Elsevier Science Publishers B.V. Amsterdam NL; U. J. Krull et al "Lipid membrane technology for chemical and biosensor development".

Journal of Physics E. Scientific Instruments, vol. 19, No. 4, Apr. 1986, pp. 271–274, The Institute of Physics, Bristol, GB: C. Hamilton et al "A gas analyzer based on the quartz crystal adsorption technique".

Analytical Chemicstry vol. 58, No. 6, May 1986, pp. 1206–1209, American Chemical Society, Wash. D.C. US: M. Thompson "Liquid–phase piezoelectric and acoustic transmission studies of interfacial immunochemistry".

"Immobilization of Ammonium bilayer membranes by complexation with anionic polymers" Toyoki Kunitake, Akihiko Tsuge, and Naotoshi Nakashima Department of Organic Synthesis, Faculty of Engineering, Kyushu University, 1984 Chemistry Letters, pp. 1783–1786, 1984.

*Primary Examiner*—Timothy M. McMahon
*Attorney, Agent, or Firm*—Cushman, Darby & Cushman

[57] ABSTRACT

Disclosed are a method of detecting bitter or odor odorous substances, which method comprises adsorbing the bitter or odorous substances onto an immobilized bilayer film and directly, quantitatively, separately, and selectively detecting the adsorbed bitter or odorous substances, and an apparatus therefor.

25 Claims, 12 Drawing Sheets

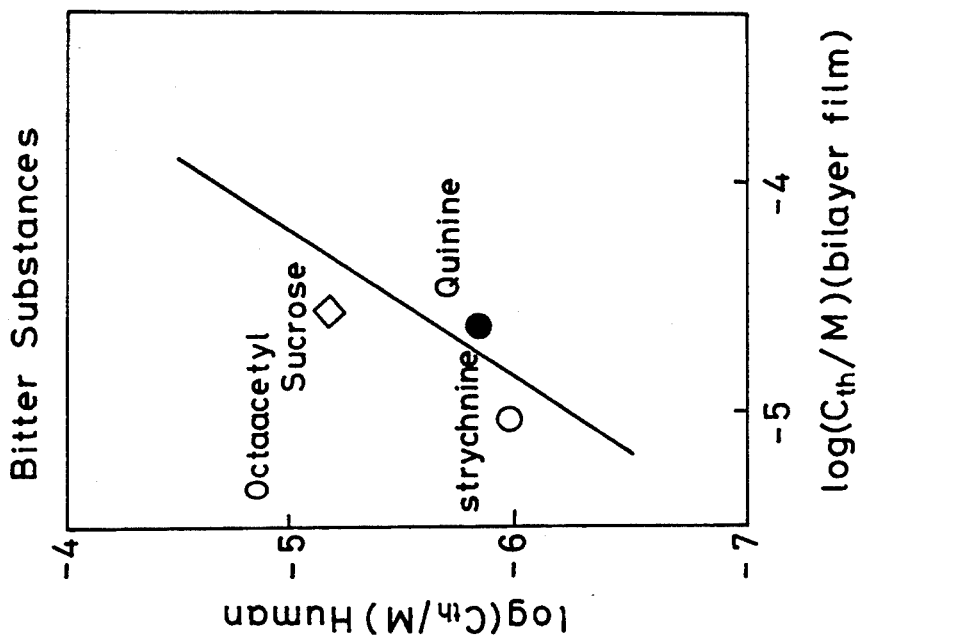
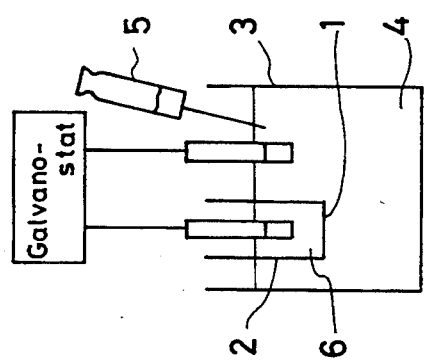
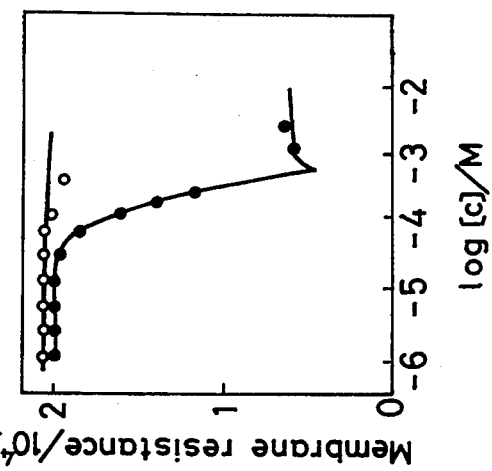
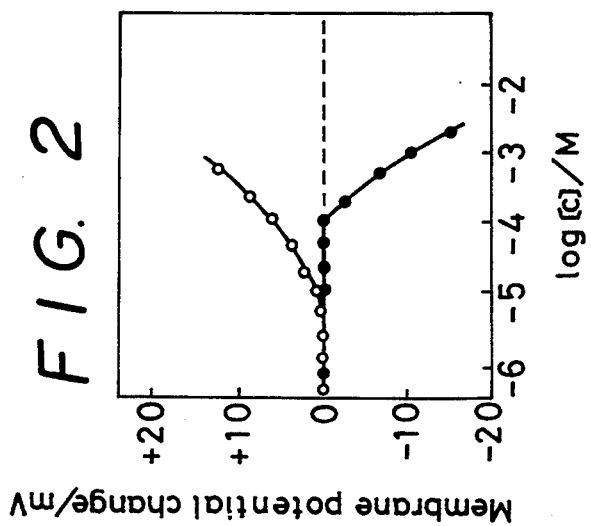

METHOD OF DETECTING BITTER OR ODOROUS SUBSTANCES AND APPARATUS THEREFOR

This is a continuation of application Ser. No. 07/666,437, filed on Mar. 11, 1991, which was abandoned upon the filing hereof which was a continuation of 07/167,310, filed Mar. 11, 1988, now abandoned.

BACKGROUND OF THE INVENTION (1) Field of the Invention

This invention relates to a method of quantitatively detecting bitter or odorous substances and an apparatus therefor.

(2) Description of the Prior Art

No method of directly detecting bitter or odorous substances has been proposed so far, but the bitter or odorous substances have been sensed by gustatory cells in humans.

A method of detecting odorous substances by gas chromatography is known, but tends to result in a chromatograph with so many peaks that it is difficult to analyze them. Reactive sensors have been practically used for special malodorants among odorous substances such as detection of alcohol by use of metal oxide and detection of propane gas by reaction with —SH group. However, no method of directly and quantitatively detecting a large number of odorous substances including the above malodorants is known. One thousand or more bitter and odorous substances exist, and it is highly desirable to develop any method of selectively detecting them.

In "Science, 54, No. 11, pages 669–678 (1984), Kenzo Kurihara", for example, a mechanism has been proposed, in which bitter substances are adsorbed onto the lipid bilayer moiety of the micro-villi membrane (hereinafter referred to as the taste receptor membrane) consisting of the lipid bilayer and various kinds of proteins in taste cells with the result that a cell potential of the taste cell is depolarized to release transfer substances and that the transfer substance acts on the taste nerve end to generate impulse for sensing bitter substances. On the other hand, a mechanism has been proposed, in which odorous substances are adsorbed onto the lipid bilayer moiety of the olfactory receptor membrane composed of the lipid bilayer and various kinds of proteins in olfactory cells with the result that depolarization takes place and impulse is generated from the olfactory nerve to sense odorous substances.

SUMMARY OF THE INVENTION

It is an object of this invention to provide a method of directly, quantitatively, selectively and easily detecting bitter or odorous substances without effecting the conventional organoleptic test, and a simple and effective apparatus therefor.

It is another object of this invention to provide a method of detecting bitter or odorous substances and an apparatus therefor, which are capable of separately and selectively detecting respective components of a mixture of bitter or odorous substances in real time with pattern recognition by use of a plurality of simple and effective apparatuses therefor.

It is another object of this invention to provide a method of detecting bitter or odorous substances and an apparatus therefor, which are capable of quantitatively detecting bitter or odorous substances with precision on the odorous of 1 to 10 nanograms by a simple method and apparatus.

That is, the present invention provides a method of detecting bitter or odorous substances, which method comprises adsorbing the bitter or odorous substances onto an immobilized bilayer film and detecting the adsorbed bitter or odorous substances.

Preferably, the present invention provides a method of detecting bitter or odorous substances, which method comprises adsorbing the bitter or odorous substances onto an immobilized bilayer film, and measuring the resulting changes due to adsorption in membrane potential and/or membrane resistance to detect the bitter or odorous substances.

Preferably, the present invention provides a method of detecting bitter or odorous substances, which method comprises adsorbing bitter or odorous substances onto an immobilized bilayer film cast on an electrode of a crystal oscillator or a piezoelectric crystal (hereinafter referred to as simply a crystal), and measuring a decreased amount in frequency of the crystal oscillator due to the adsorption of the bitter or odorous substances to detect the bitter or odorous substances adsorbed.

The present invention provides an apparatus for detecting bitter or odorous substances, which apparatus comprises an immobilized bilayer film to adsorb the bitter or odorous substances thereonto and a means of measuring the resulting changes due to adsorption of the bitter or odorous substances in membrane potential and/or membrane resistance.

The present invention provides an apparatus for detecting bitter or odorous substances, which apparatus comprises a frequency measuring means composed of a crystal oscillator and an immobilized bilayer film cast on an electrode of the crystal oscillator, decreased amounts of frequency due to the adsorption of the bitter or odorous substances onto the immobilized bilayer film being measured.

BRIEF DESCRIPTION OF THE DRAWINGS

FIG. 1 is a schematic view of an apparatus for measuring membrane potential and/or membrane resistance in a first preferred embodiment of the present invention, FIG. 2 is a graph showing the result of the measurement of the membrane potential, FIG. 3 is a graph showing the result of the measurement of the membrane resistance, FIG. 4 is a graph showing correlation between threshold concentration of adsorption for bitter substances and threshold value in humans.

DETAILED DESCRIPTION OF THE INVENTION

Figure 5:
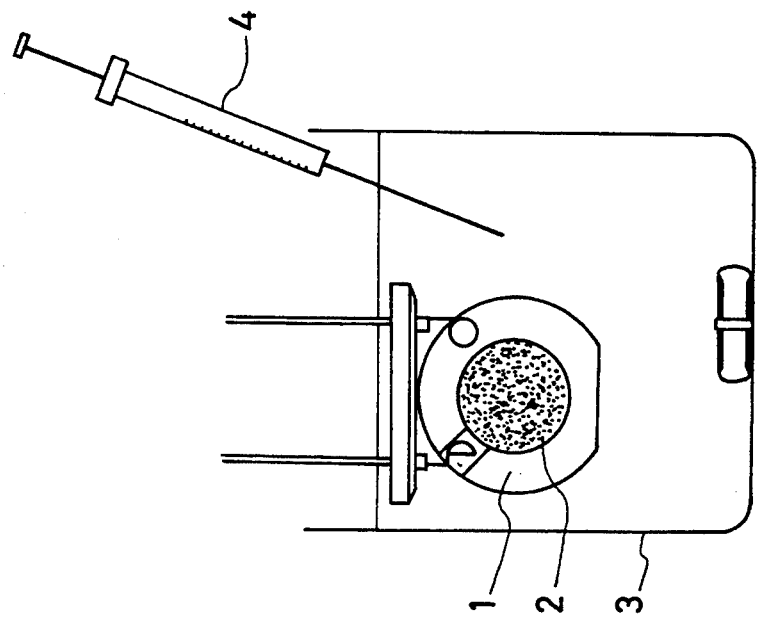
FIG. 5 is a graph showing correlation between threshold concentration of adsorption for odorous substances and threshold value in frog.

The bitter substances used in the present invention are not specifically limited so long as they are adsorbed onto the immobilized bilayer film of the present invention, and may include acids, salts, etc.

The typical examples of the bitter substances include strychnine, quinine, nicotine, phenylthiourea, papaverine, caffeine, naringin, octaacetyl sucrose, and the like. The odorous substances used in the present invention are not specifically limited so long as they are adsorbed onto the immobilized bilayer film of the present invention, and may include perfumes, anesthetics, malodorants, and the like.

The typical examples of the odorous substances include β-ionone, aliphatic alcohols such as octanol, camphor, amylacetate, vanilline, ethylbutylate, phenol, aldehydes, and the like.

Typical examples of the perfumes include P-anisaldehyde, 1-undecanol, anisalcohol, anisol, phenylethyl acetate, citral, methyl salicylate, benzyl acetate, tetrahydrogeraniol, terpineol, geranyl acetate, and the like.

Examples of the general anesthetics as the compounds having narcosism in the aforementioned anesthetics are shown in Table 3. In Table 3, potency is a value representing intensity of the anesthetics and is shown as values obtained by use of a tadpole.

TABLE 3

| No. | Anesthetic Compounds | Potency |
|---|---|---|
| 1 | methanol | 1.00 |
| 2 | ethanol | 2.43 |
| 3 | acetone | 3.47 |
| 4 | 1-propanol | 9.43 |
| 5 | butanone | $1.20 \times 10$ |

TABLE 3-continued

| No. | Anesthetic Compounds | Potency |
|---|---|---|
| 6 | diethyl ether | $2.99 \times 10$ |
| 7 | 1-butanol | $4.43 \times 10$ |
| 8 | paraldehyde | $5.44 \times 10$ |
| 9 | benzylalcohol | $5.01 \times 10^2$ |
| 10 | chloroform | $7.62 \times 10^2$ |
| 11 | 1-hexanol | $1.12 \times 10^3$ |
| 12 | halothane | $4.47 \times 10^3$ |
| 13 | methoxyflurane | $4.86 \times 10^3$ |
| 14 | 1-octanol | $7.93 \times 10^3$ |
| 15 | pentane | $1.51 \times 10^4$ |
| 16 | 1-nonanol | $4.03 \times 10^4$ |
| 17 | hexane | $6.75 \times 10^4$ |
| 18 | 1-decanol | $1.00 \times 10^5$ |

Examples of the malodorants include malodor-emitting substances selected from ketones, amines, imines, aldehydes such as acetaldehyde, organic acids and the like, sulfur compounds such as methyl mercaptan, hydrogen sulfide, methane sulfide, methyl disulfide and the like, styrene, mixtures thereof, malodor-emitting substances selected from various kinds of industrial wastes and mixtures thereof, foul breath-producing substances and mixtures thereof, and the like.

The immobilized bilayer film used in the present invention include those prepared by immobilizing, by use of polymers, (i) synthetic lipids such as ammonium salts, sulfonates, carboxylates in the form of trialkyl, dialkyl and/or monoalkyl as represented by the formula:

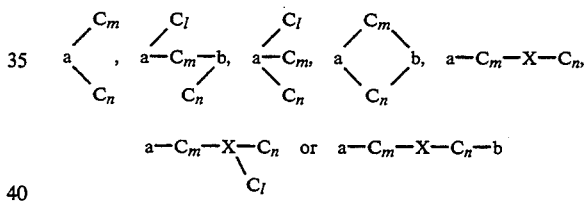

where a and b represent a hydrophilic group moiety such as $-N^+(CH_3)_3$, $-SO_3^-$, $PO_4^-$, polyol, polyether or the like, $C_l$, $C_m$ and $C_n$ represent a hydrophobic group moiety such as alkyl group, fluoroalkyl group, alkylene group having a $C_8$ or higher carbon chain, or the like, and X represents a rigid segment such as diphenylazomethylene group, biphenyl group, naphthalene group, anthracene group or the like, and/or (ii) natural lipids such as phosphatidyl choline, phosphatidyl serine and the like.

Specific examples of the immobilized bilayer film used in the present invention include (i) films prepared by blending the synthetic lipid and/or natural lipid with high-molecular compounds such as polyvinyl chloride, polystyrene, polycarbonate, polyvinyl alcohol, acetyl cellulose and the like, followed by casting; (ii) films prepared by impregnating pores of filters having a microporous structure such as miliporefilter, duraguird, and the like, with a chloroform solution of the synthetic lipid and/or natural lipid, followed by drying; (iii) films obtained by dissolving a polyion complex powder prepared by mixing an aqueous dispersion of the synthetic lipid and/or natural lipid having a cationic, hydrophilic group with an aqueous solution of an anionic high-polymer such as polystyrene sulfonic acid, heparin, polyvinyl-sulfonic acid, polyacrylic acid, polyglutamic acid, and the like in chloroform, followed by casting;

(iv) polyion complex type bilayer films composed of the lipid having an anionic hydrophilic group and cationic high polymer such as polyallylamine, polyethylene imine, quaternary polyaminostyrene and the like; and
(v) Langmuir-Blodgett type multibilayer films composed of the synthetic lipid and/or natural lipid.

The crystal oscillator or the piezoelectric crystal used in the present invention may include the crystal oscillator or the piezoelectric crystal conventionally used as a sensor for sulfur dioxide, ammonia gas, etc., and SAW device. A microbalance having a sensitivity of the order of nanogram may also be used in place of the crystal oscillator or the piezoelectric crystal.

Thus, the present invention makes it possible to directly, quantitatively, selectively and easily detect bitter or odorous substances without effecting the conventional organoleptic test.

The present invention also makes it possible to directly, quantitatively selectively and easily detect odorous substances both in the aqueous phase and gas phase in place of the conventional method using living bodies as samples and living things for detection of odorous substances.

The present invention also makes it possible to quantitatively detect bitter or odorous substances with precision on the order of 1 to 10 nanograms by a simple method and apparatus.

The present invention also makes it possible to separately and selectively detect respective components of a mixture of bitter or odorous substances in real time with pattern recognition by use of a plurality of simple and effective apparatuses therefor.

The present invention will be described more in detail with reference to drawings and Examples.

A first embodiment of the apparatus for detecting bitter or odorous substances in the present invention is explained with reference to FIG. 1. In FIG. 1, element 1 is an immobilized bilayer film, which is mounted at the end of polyethylene tube 2, for example, and is arranged between an inner aqueous phase 6 free of bitter or odorous substances and an outer aqueous phase containing bitter or odorous substances injected from bitter or odorous substances injecting device 5, and both measuring probes of the galvanostat for means of measuring the membrane potential or membrane resistance are inserted into the outer aqueous phase 4 and the inner aqueous phase 6 respectively. In FIG. 1, element 3 is a cell containing outer aqueous phase 4. The membrane potential is measured, for example, by use of a Ag-/AgCl/KCl$_{sat}$ electrode with the inner aqueous phase 6 containing 5 mM NaCl and the outer aqueous phase 4 containing 0.5 mM NaCl. The membrane resistance is measured, for example, by LCR meter by use of a platinum electrode with the inner and outer aqueous phases both containing 0.1M NaCl.

Figure 6:
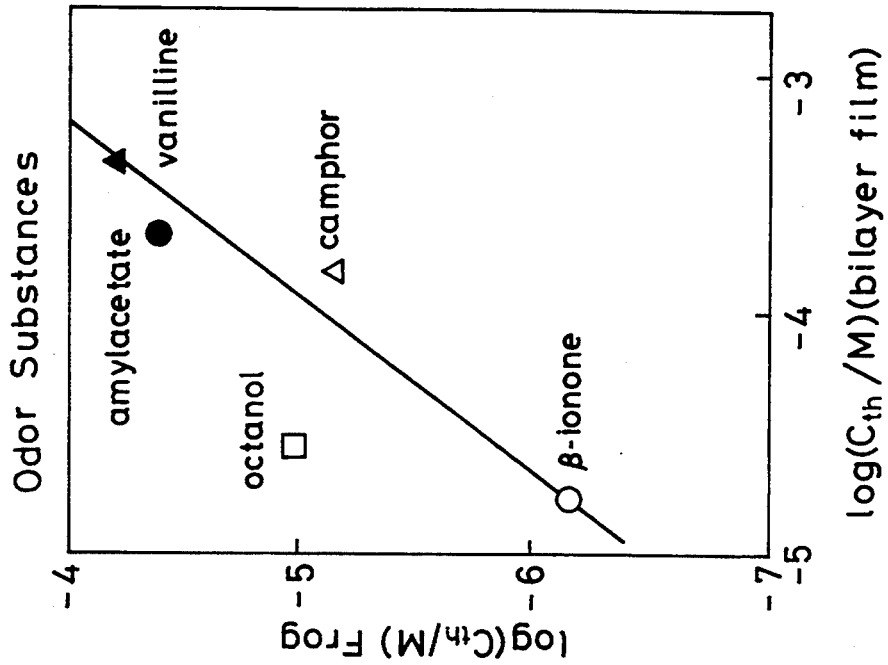
FIG. 6 is a schematic view of an apparatus for measuring a decreased amount in frequency of the crystal oscillator in a second preferred embodiment of the present invention.

A second embodiment of the apparatus for detecting bitter or odorous substances in the present invention is explained with reference to FIG. 6. In FIG. 6, the immobilized bilayer film is cast on a silver-deposited electrode 2 of the crystal oscillator 1 [or on both sides of a silver-electrode-deposited piezoelectric crystal (9 MHz; AT-cut)] and dipped into deionized water in cell 3, bitter or odorous substances are injected thereinto as a solution thereof through an irritant-injecting device 4, frequency changes after the injection are measured by a frequency measuring means (not shown) constituting the crystal oscillator 1, and adsorbed amounts of bitter or odorous substances onto the immobilized bilayer film are determined from proportionality thereof to the frequency changes thus obtained.

Selectivity of bitter or odorous substances to types of the bilayer constituting the immobilized bilayer film makes it possible to separately and selectively detect respective components of a mixture of bitter or odor substances in real time with pattern recognition by use of a plurality of detecting apparatuses comprising immobilized bilayer films having different bilayers respectively.

EXAMPLE 1

An example of the method of detecting bitter or odorous substances in the present invention is more specifically explained with reference to FIGS. 1-5.

In FIG. 1, an immobilized bilayer film 1 obtained by casting a polyion complex between dialkyl ammonium salt ion ($2C_{18}N^+2C_1$) and polystyrene sulfonic acid ion ($PSS^-$) [or an immobilmzed $2C_{18}N^+2C_1/PSS^-$ bilayer film 1 prepared as a polyion complex from dioctadecyl-dimethyl-ammonium bromide $2C_{18}N^+2C_1Br^-$ and sodium poly(styrenesulfonate) ($PSS^-Na^+$)] is cast from chloroform solution on both sides of a silver-electrode-deposited piezoelectric crystal 2 (9 MHz; AT-cut). The cast film is mounted at the end of a polyethylene tube 2 and dipped into deionized water in 50 ml cell 3. Bitter or odorous substances are injected into the outer aqueous phase 4 through irritant-injecting device 5 and the resulting membrane potential is measured by use of a Ag/AgCl/KCl$_{sat}$ electrode with the inner aqueous phase 6 containing 5 mM NaCl and the outer aqueous phase 4 containing 0.5 mM NaCl. The membrane resistance is measured by LCR meter by use of a platinum electrode with the inner and outer aqueous phases both containing 0.1M NaCl. Papaverine as the bitter substance and octanol as the odorous substance are added at varied concentrations respectively, and the resulting membrane potential changes and membrane resistance changes are shown in FIG. 2 and FIG. 3 respectively. FIGS. 2 and 3 show that addition of the bitter substances such as papaverine results in little or no changes in membrane resistance in the measured concentration range of $10^{-6}$–$10^{-3}$M, and that the membrane potential only changes at concentrations of $10^{-5}$M or higher. This shows that the membrane potential change due to adsorption of bitter substances is mainly caused by interfacial potential. On the other hand, addition of odorous substances such as octanol results in simultaneous changes in membrane potential and membrane resistance in the concentration range of $10^{-4}$M or higher. This suggests that adsorption of odorous substances such as octanol results in disturbing the structure of the bilayer film to reduce membrane resistance, and that membrane potential changes are produced by diffusion potential changes.

As shown in FIG. 4, the threshold concentrations causing membrane potential changes for bitter substances by use of the immobilized bilayer film correspond very well to threshold values in humans. As shown in FIG. 5, the threshold concentrations causing membrane potential changes for odorous substances correspond very well to membrane potential-producing threshold values of olfactory cells in frog.

This makes it possible to detect bitter substances by adsorbing bitter substances onto the immobilized bilayer film, for example, followed by measuring the resulting membrane potential changes due to the adsorption, and to detect odorous substances by adsorbing odorous substances onto the immobilized bilayer film, followed by measuring changes in membrane potential and/or membrane resistance due to the adsorption.

The immobilized bilayer film is prepared, for example, by a process in which dialkylammonium salt ion and polystyrenesulfonic acid ion are reacted at 70° C. to form precipitates of polyion complex followed by reprecipitation and drying, and the resulting precipitates are dissolved in chloroform to be cast on a substrate.

EXAMPLE 2

Figure 8:
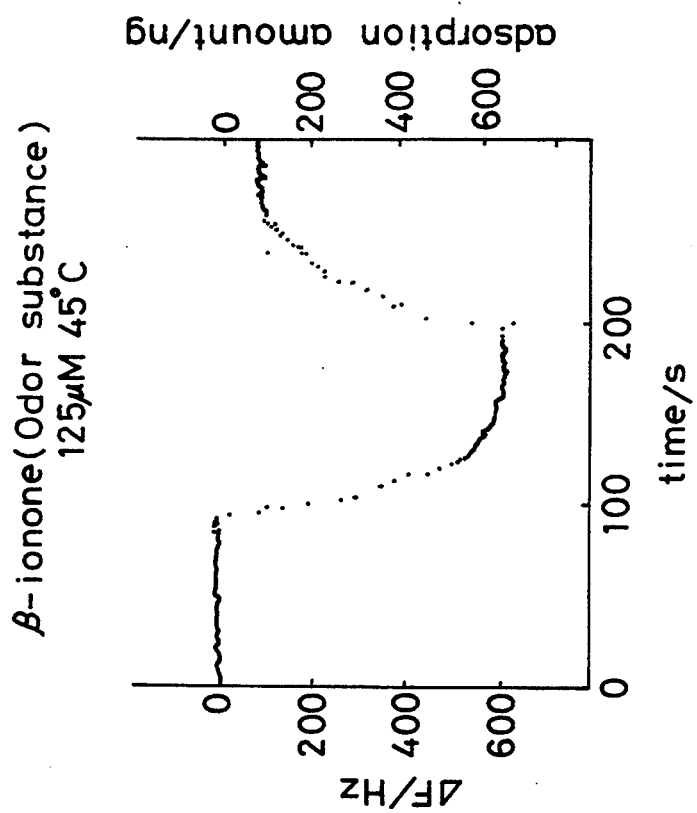
FIG. 8 is a graph showing changes with time of frequency changes and adsorption amounts for odorous substances.
Figure 7:
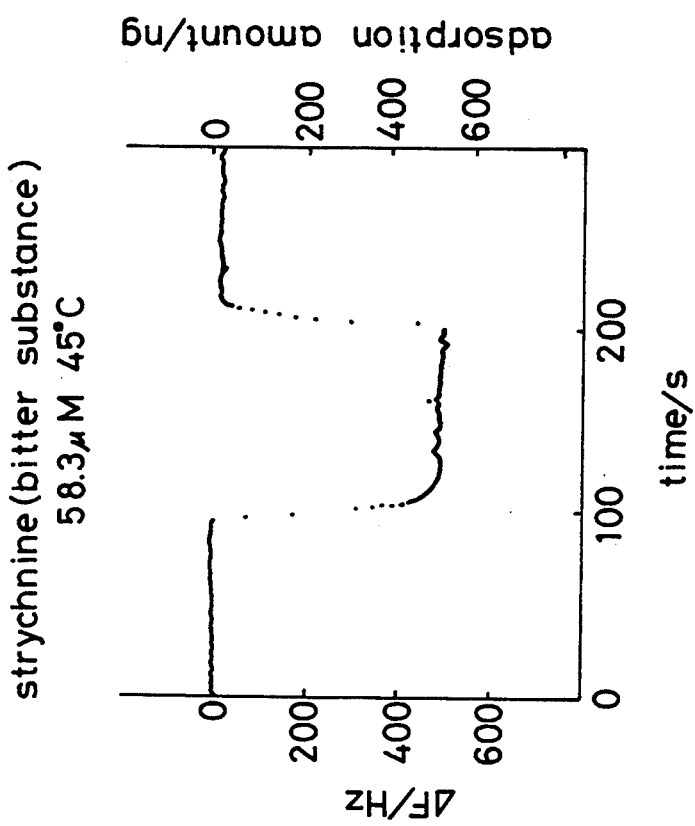
FIG. 7 is a graph showing changes with time of frequency changes and adsorption amounts for bitter substances.

As shown in FIG. 6, the same immobilized $2C_{18}N^+2C_1/PSS^-$ bilayer film as in Example 1 is cast from chloroform solution on both sides of a silver-electrode deposited piezoelectric crystal 2 (9 MHz; AT-cut) or on a silver-deposited electrode 2 of the crystal oscillator 1 to a thickness of 0.5 μm, followed by being dipped into deionized water in 50 ml cell 3. An ethanol solution of strychnine as the bitter substance or of β-ionone as the odorous substance is injected through an irritant-injecting device 4 to measure frequency changes due to injection, and to determine adsorbed amounts onto the immobilized bilayer film from proportionality thereof to frequency changes respectively. Measurements are made at 45° C. and a concentration of 58.3 μM for strychnine, and at 45° C. and a concentration of 125 μM for β-ionone. FIG. 7 and FIG. 8 show frequency changes and adsorption amounts calculated therefrom with time respectively. As shown in FIG. 7 and FIG. 8, the crystal oscillator is removed from the cell and dipped into distilled water in a separate cell 200 seconds after starting the measurements with the result that desorption of the adsorbed strychnine or β-ionone is observed. This shows that adsorption of bitter substances such as strychnine and that of odorous substances such as β-ionone are both reversible, and that the crystal oscillator may be used repeatedly because of easy adsorption thereonto or desorption therefrom.

On the other hand, the same correlation as shown in FIG. 4 is observed between gustatory threshold values in humans and threshold concentrations ($C_{th}$), at which frequency change due to adsorption of bitter substances onto the immobilized bilayer film is observed. The same correlation as shown in FIG. 5 is observed between olfactory threshold values in frog and threshold concentrations ($C_{th}$), at which frequency change due to adsorption of odorous substances onto the immobilized bilayer film is observed. The threshold concentrations ($C_{th}$) are specific to respective bitter substances or odorous substances relative to changes in frequency of the crystal oscillator.

EXAMPLE 3

The experiments in Example 2 are repeated except that the immobilized bilayer film is in the state of liquid crystals with the result that adsorbed amounts are increased.

EXAMPLE 4

Adsorbed amounts of strychnine as the bitter substance, β-ionone as the odorous substance, sugar as the sweet substance and of glycine as the substance are measured respectively in the same manner as in Example 2, and the adsorbed amounts thus measured are shown in Table 1 in terms of partition coefficient. The partition coefficient means a ratio of the adsorbed amount of an irritant such as the bitter or odorous substance or the like onto the immobilized bilayer film to an amount by weight of the irritant such as the bitter or odorous substance or the like in the aqueous solution of a constant volume. The results in Table 1 show that adsorption onto the immobilized bilayer film of the present invention is specific and selective to the bitter and odorous substances.

TABLE 1

| Irritants | Partition Coefficient ($10^{-3}$) |
| --- | --- |
| Strychnine | 2.5 |
| β-ionone | 3.0 |
| Sugar | 0.01 |
| Glycine | 0.02 |

EXAMPLE 5

Experiments are carried out in the same manner as in Example 2 by use of strychnine as the bitter substance in the cases where the immobilized bilayer film, hydrophobic polystyrene (PSt) film, hydrophilic polyvinyl alcohol (PVA) film and polymethyl-L-glutamate (PMLG) film as polyamino acid are coated on the silver-deposited electrode 2 of the crystal oscillator or on the silver-electrode-deposited piezoelectric crystal 2 respectively, and where none are coated to measure the adsorbed amounts, and the results are shown in Table 2 in terms of partition coefficient. The results in Table 2 show that strychnine as the bitter substance is specifically and selectively adsorbed onto the immobilized bilayer film of the present invention.

TABLE 2

| Coating | Partition Coefficient ($10^{-3}$) |
| --- | --- |
| None | 0.03 |
| Immobilized bilayer film | 2.5 |
| Polystyrene film | 0.05 |
| Polyvinyl alcohol film | 0.03 |
| Polymethyl-L-glutamate film | 0.02 |

EXAMPLE 6

Figure 10:
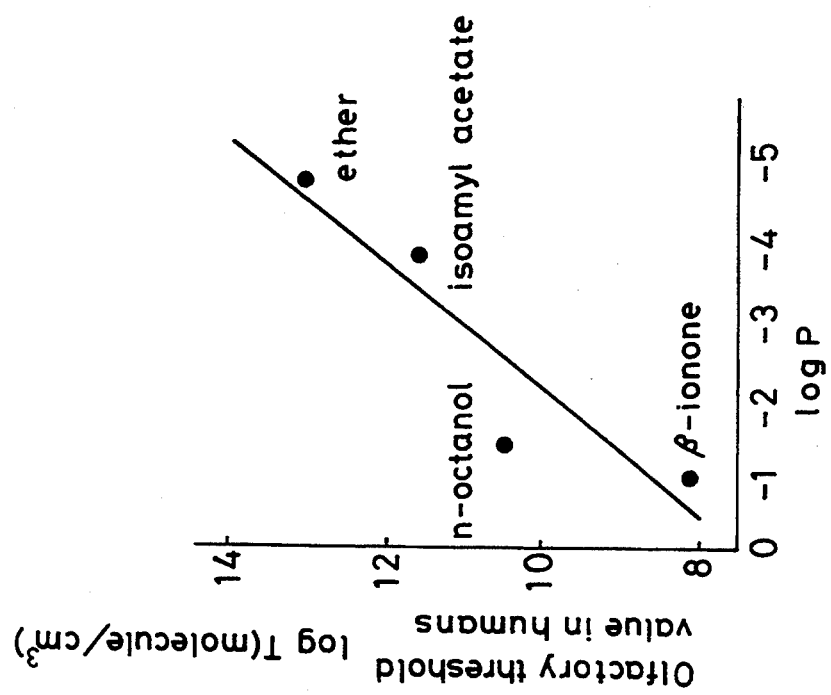
FIG. 10 is a graph showing correlation between partition coefficient and olfactory threshold value in humans.
Figure 9:
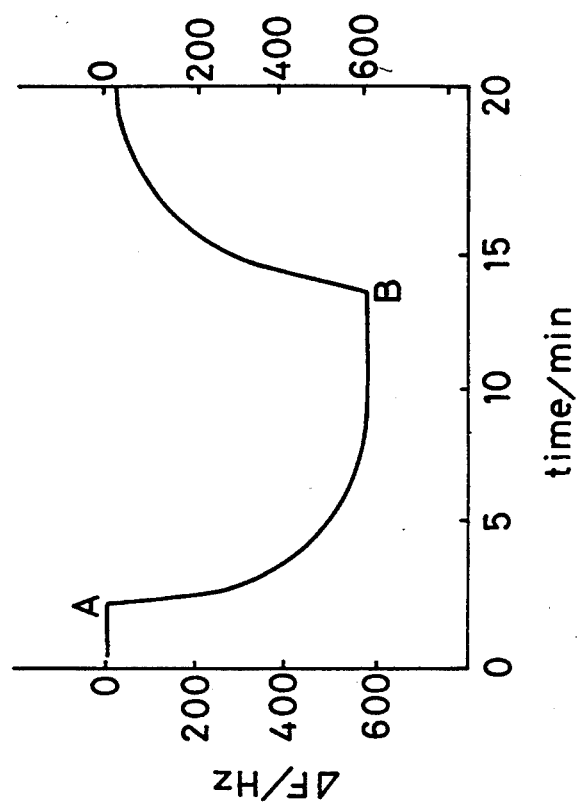
FIG. 9 is a graph showing changes with time of frequency changes and adsorption amounts for gaseous odorous substances.

The same immobilized bilayer film-coated crystal oscillator or crystal as in Example 2 is placed at point A in FIG. 9 in a cell saturated with β-ionone vapor as the odorous substance in place of the cell containing deionized water as in Example 2, and the frequency changes are measured as in Example 2 to determine the adsorbed amounts. The results are shown in FIG. 9. As shown in FIG. 9, as soon as the coated crystal oscillator or crystal is placed in the cell, the frequency rapidly decreases and then becomes constant soon. At point B in FIG. 9, the coated crystal oscillator or crystal is removed from the cell into atmosphere with the result that the frequency reverts soon to the same as at point A in FIG. 9, at which the coated crystal oscillator or crystal is placed in the cell. The same experiments as above are repeated for n-octanol, isoamylacetate and ether as other odorous substances with the same results as above. In the determination of adsorbed amounts from frequency changes thus obtained, the adsorbed amount is represented in terms of partition coefficient obtained by dividing the adsorbed amount by the total weight of the odorous substance molecules actually existing in the gas phase in order to cancel differences in vapor pressure in the gas phase. FIG. 10 shows a good correlation between the partition coefficient thus obtained and olfactory threshold values in humans.

Comparative Example 1

The same experiments as in Example 6 are repeated except that an uncoated crystal oscillator or crystal is used with the result that little or no frequency changes due to adsorption of odorous substances are observed.

Comparative Example 2

The same experiments as in Example 6 are repeated except that a crystal oscillator or crystal coated with polystyrene as the hydrophobic polymer with the result that very little frequency changes due to adsorption of odorous substances are observed.

EXAMPLE 7

Figure 11:
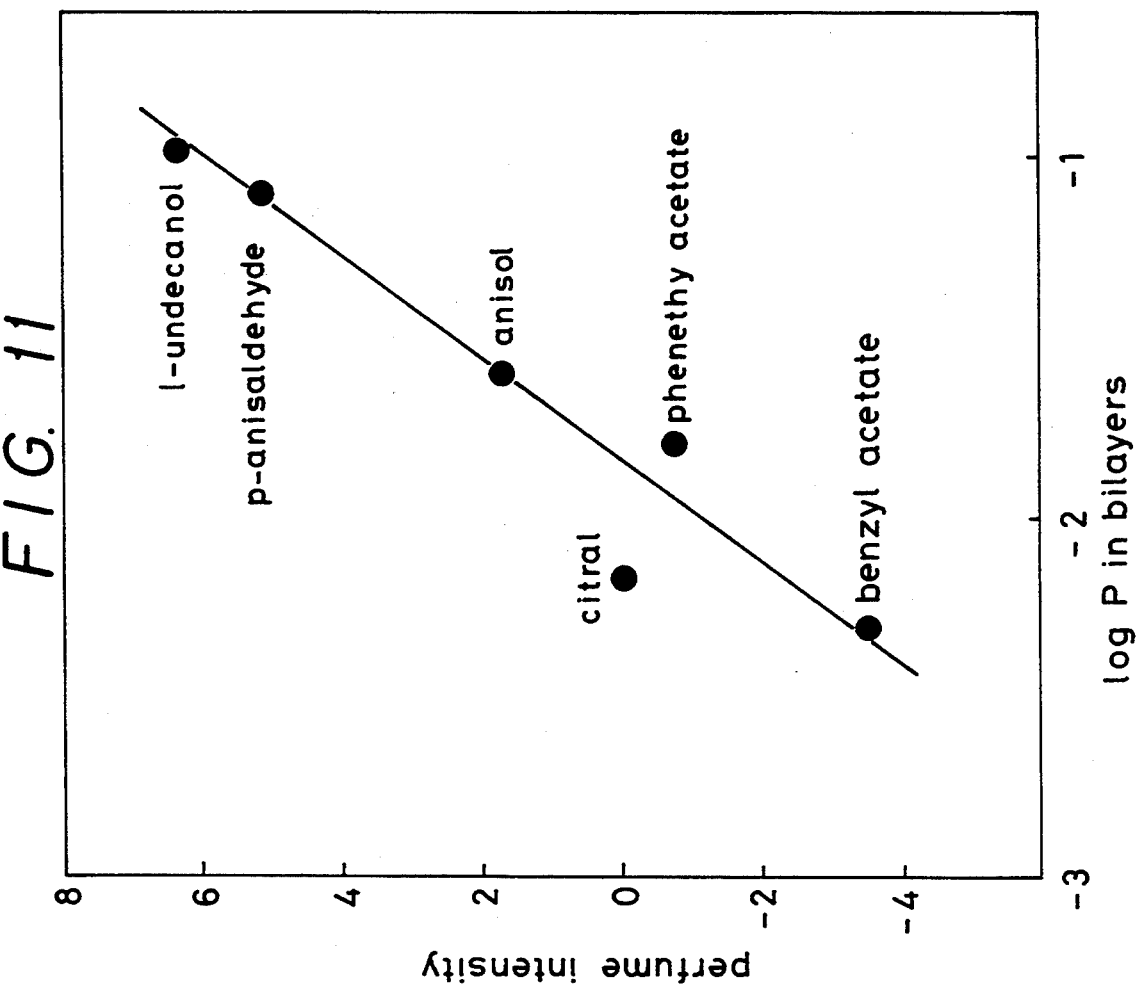
FIG. 11 is a graph showing correlation between partition coefficient and perfume intensity.

The same experiments as in Example 6 are repeated by use of benzyl acetate, phenethyl acetate, citral, anisol, p-anisaldehyde and 1-undecanol selected from perfumes as odor substances. The results are shown in FIG. 11. FIG. 11 shows a good correlation between logarithm of partition coefficient (log P) and perfume intensity relative to the immobilized bilayer film. The perfume intensity means an intensity determined in such a manner that a perfume sniffs odors emitted from respective dialkylphthalate solutions of perfumes and empirically determines intensities of respective primary odors on the basis of citral as the perfume.

EXAMPLE 8

Figure 12:
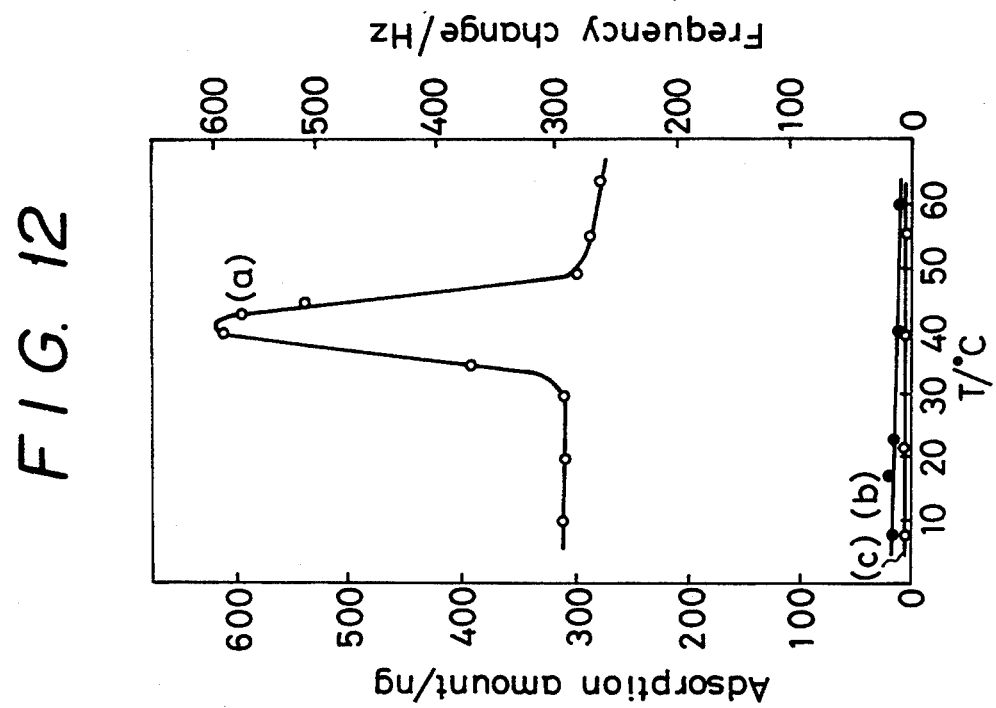
FIG. 12 is a graph showing correlation of adsorbed amount and frequency change to temperature.

Experiments are repeated in the same manner as in Example 2 to show the temperature dependence of the frequency change and adsorption amount of strychnine as the bitter substance in the aqueous solution containing 19.3 p.p.m. of strychnine. The results are shown in FIG. 12. FIG. 12 shows that adsorption on the $2C_{18}N^+2C_1/PSS^-$ bilayer-coated crystal or crystal oscillator is high and specifically increased near 40°–45° C., close to the phase transition temperature (Tc=45° C.) of the lipid bilayer on the crystal or the crystal oscillator. Similar temperature dependence is observed on addition of various odorous substances and bitter substances other than strychnine, and that these substances are specifically adsorbed at temperatures near $T_c$, where solids coexist with fluid liquid crystals in the lipid bilayers.

Comparative Example 3

The same experiments as in Example 8 are repeated except for using an uncoated crystal oscillator or piezoelectric crystal with the result that little or no frequency changes due to adsorption of strychnine are observed regardless of the temperature employed. The results are shown in FIG. 12. Similar temperature dependence is observed on addition of various odorous substances and bitter substances other than strychnine.

Comparative Example 4

The same experiments as in Example 8 are repeated except for using a hydrophobic polystyrene-coated crystal oscillator or piezoelectric crystal with the result that very little frequency changes due to adsorption of strychnine are observed regardless of the temperature employed. The results are shown in FIG. 12. Similar temperature dependence is observed on addition of various odorous substances and bitter substances other than strychnine.

EXAMPLE 9

Experiments are repeated in the same manner as in Example 2 at 45° C. in the state of liquid crystals and at 20° C. in the crystalline state respectively in an aqueous solution of halothane as the anesthetics at a concentration of $9.48 \times 10^{-4}$(M). The results are shown in Table 4. The results show that adsorbed amounts are increased when the coated film is in the state of liquid crystals.

EXAMPLE 10

Experiments of Example 9 are repeated except that cholesterylammonium poly(p-styrenesulfonate) is used as the immobilized bilayer film. The results are shown in Table 4.

EXAMPLE 11

Experiments of Example 9 are repeated except that cetyl trimethylammonium poly(p-styrenesulfonate) ($CTAB^+/PSS^-$) is used as the immobilized bilayer film. The results are shown in Table 4.

Comparative Example 5

Experiments of Example 9 are repeated at 45° C. except that a hydrophobic polystyrene film in place of the $2C_{18}N^+2C_1/PSS^-$ film is used as the coated film. The results are shown in Table 4.

Comparative Example 6

Experiments of Example 9 are repeated at 45° C. except that a hydrophobic polyvinylchloride film in place of the $2C_{18}N^+2C_1/PSS^-$ film is used as the coated film. The results are shown in Table 4.

Comparative Example 7

Experiments of Example 9 are repeated at 45° C. except that a hydrophilic polyvinyl alcohol film in place of the $2C_{18}N^+2C_1/PSS^-$ film is used as the coated film. The results are shown in Table 4.

Comparative Example 8

Experiments of Example 9 are repeated except that a film of poly($\gamma$-methyl-L-glutamate) as polyamino acid in place of the $2C_{18}N^+2C_1/PSS^-$ film is used. The results are shown in Table 4.

TABLE 4

| | Coated films | Frequency Changes-$\Delta F$/Hz | Adsorbed amounts/ng | Partition coefficients P |
|---|---|---|---|---|
| Example 9 | Polyion complex film $2C_{18}N^+2C_1/PSS^-$ (45° C.) | 303 | 318 | 85.2 |
| | (20° C.) | 96 | 101 | 26.9 |
| Example 10 | Cholesterylammonium poly(p-styrenesulfonate) | 78 | 82 | 21.9 |
| Example 11 | $CTAB^+/PSS^-$ | 237 | 249 | 66.6 |
| Comparative | Hydrophobic polymer Polystyrene [Pst] | 70 | 74 | 19.6 |

TABLE 4-continued

| Coated films | | Frequency Changes- ΔF/Hz | Adsorbed amounts/ng | Partition coefficients P |
| --- | --- | --- | --- | --- |
| Example 5 | | | | |
| Comparative Example 6 | Polyvinyl chloride [PVC] | 70 | 74 | 19.6 |
| Comparative Example 7 | Hydrophilic polymer Polyvinyl alcohol [PVA] | 50 | 53 | 14.0 |
| Comparative Example 8 | Polyamino acid Poly(γ-methyl-L-glutamate) [PMLG] | 168 | 176 | 47.1 |

EXAMPLE 12

Figure 14:
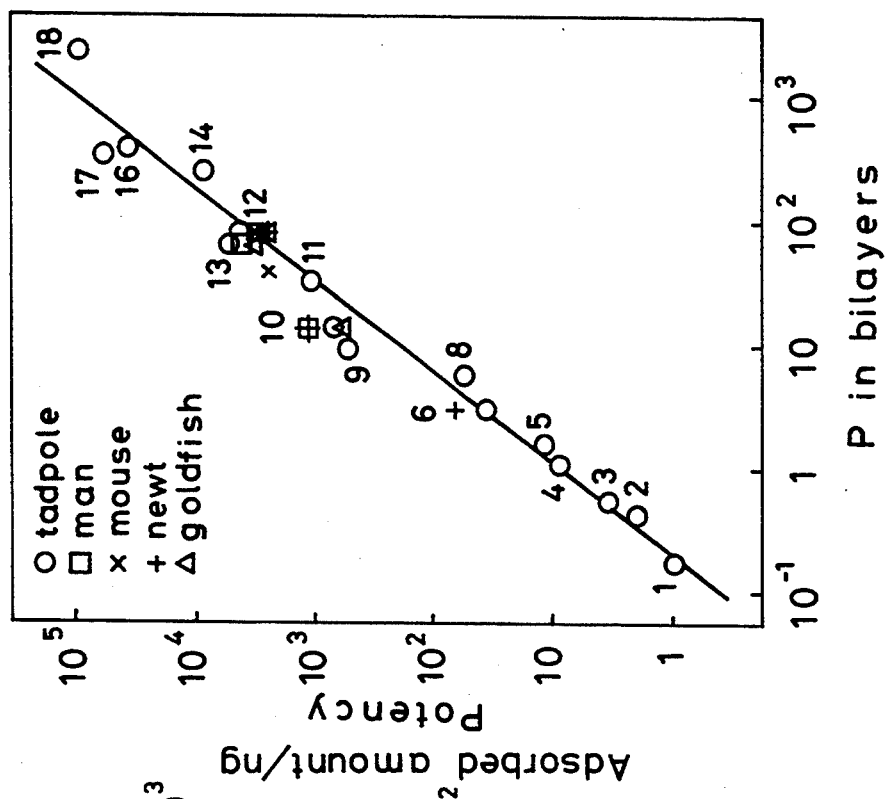
FIG. 14 is a graph showing correlation between partition coefficient and potency.
Figure 13:
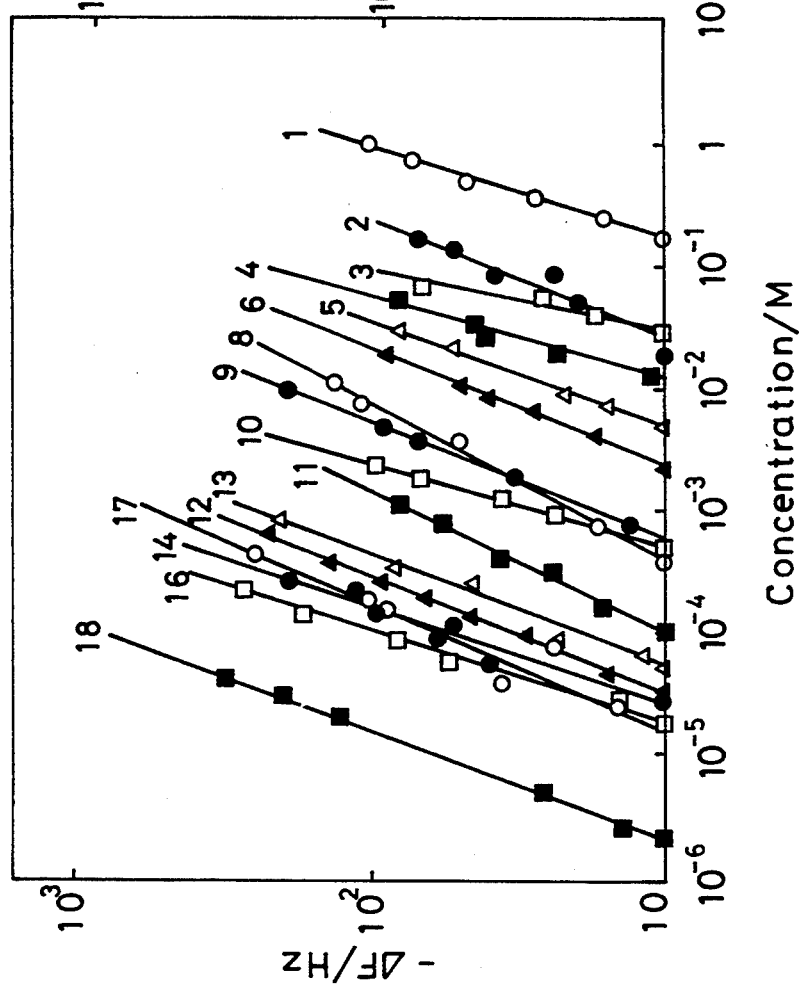
FIG. 13 is a graph showing correlation of adsorbed amount and frequency change to concentration.
Figure 16:
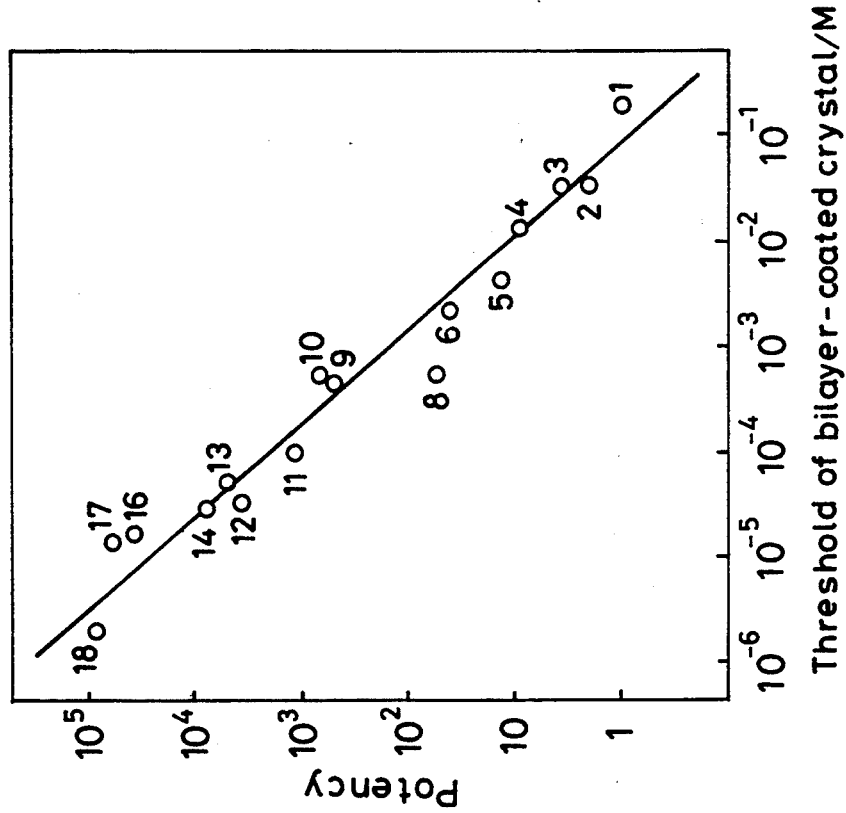
FIG. 16 is a graph showing correlation between threshold value and potency.
Figure 15:
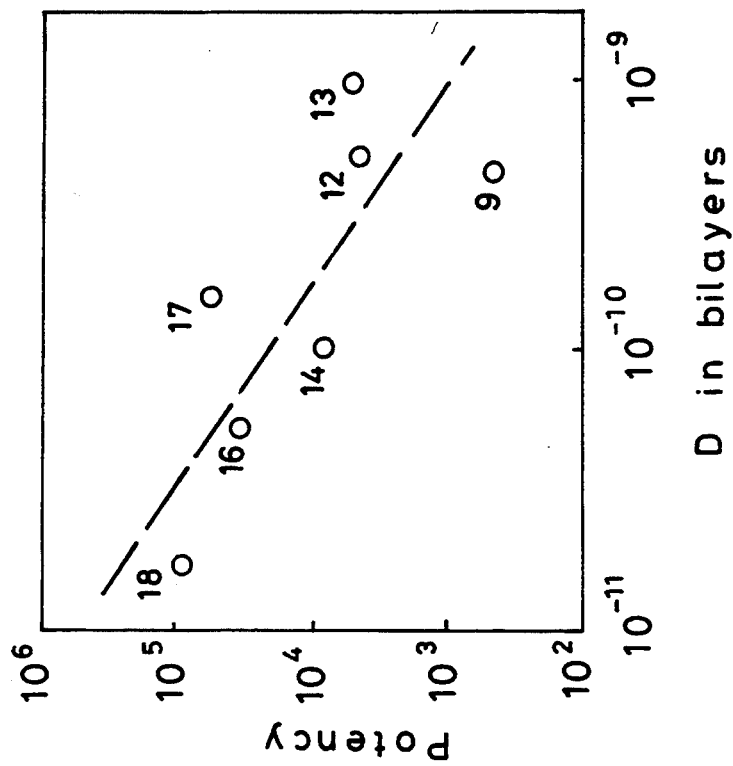
FIG. 15 is a graph showing correlation between diffusion coefficient and potency.

Experiments of Example 2 are repeated by using 18 anesthetics as shown in Table 3 respectively at varied concentrations. The results are shown in FIG. 13. Respective figures in FIG. 13 represent the numbers of respective anesthetic compounds. Since frequency changes of 10 Hz or less are considered to be within errors in measurements, the concentration at the frequency change of 10 Hz is defined as a concentration threshold value. As shown in FIG. 13, as the concentration is increased, the adsorbed amounts linearly increase, and this means that the partition coefficient shows a constant value above the threshold value. Correlation between the partition coefficient thus obtained and the potency of respective anesthetics shown in Table 3 is shown in FIG. 14. Similarly, correlation between the diffusion coefficient D and the potency in the tadpole is shown in FIG. 15. Correlation between the threshold value and the potency in the tadpole is shown in FIG. 16.

FIG. 14 shows a good correlation (coefficient of correlation $\gamma=0.988$) between potency and partition coefficient. This shows that the anesthetic having increased partition coefficient has increased intensity as the anesthetic too, and it may be said that this strongly suggests production of narcosism by direct adsorption of the an esthetic onto the lipid film.

EXAMPLE 13

Figure 17:
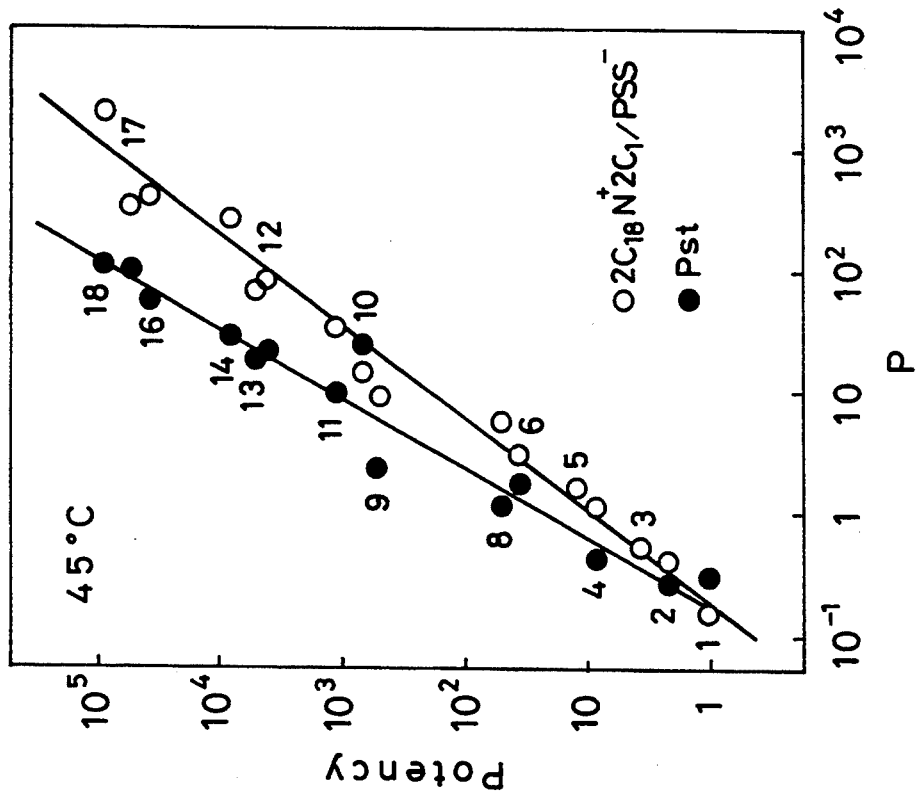
FIG. 17 and FIG. 18 are graphs showing correlation between partition coefficient and potency respectively.

Adsorption experiments are carried out in the same manner as in Example 12 at 45° C. in the state of liquid crystals and 20° C. in the crystalline state. Correlation between the logarithm of partition coefficient P and the logarithm of potency in the tadpole is shown in FIG. 17. FIG. 17 shows a good correlation (coefficient of correlation $\gamma=0.961$) between potency and partition coefficient at 20° C. in the crystalline state, but shows that the above correlation is poor compared with that (coefficient of correlation $\gamma=0.988$) at 45° C. in the state of liquid crystals, and that the partition coefficients at 20° C. are less, as a whole, than those at 45° C. It may be said that this suggests direct action of the anesthetic onto the lipid in the membrane of the living body in the state of liquid crystals.

Comparative Example 9

Figure 18:
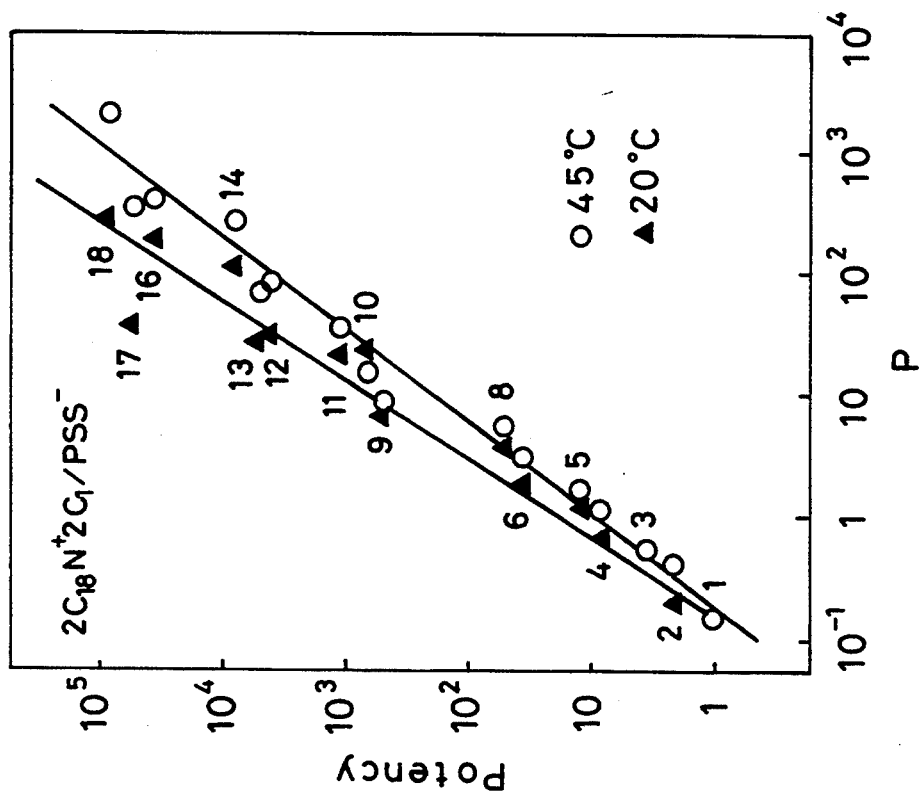

Adsorption experiments of anesthetics in the same manner as in Example 12 by use of a hydrophobic polystyrene film in place of the $2C_{18}N^{+}2C_1/PSS^{-}$ film. Correlation between partition coefficient P and potency in the tadpole is shown in FIG. 18 along with the results in Example 12. Coefficient of correlation for the polystyrene film is 0.901 and less than that (0.988) for the $2C_{18}N^{+}2C_1/PSS^{-}$ film, resulting in poor correlation compared with that for the $2C_{18}N^{+}2C_1/PSS^{-}$ film.

EXAMPLE 14

Figure 19:
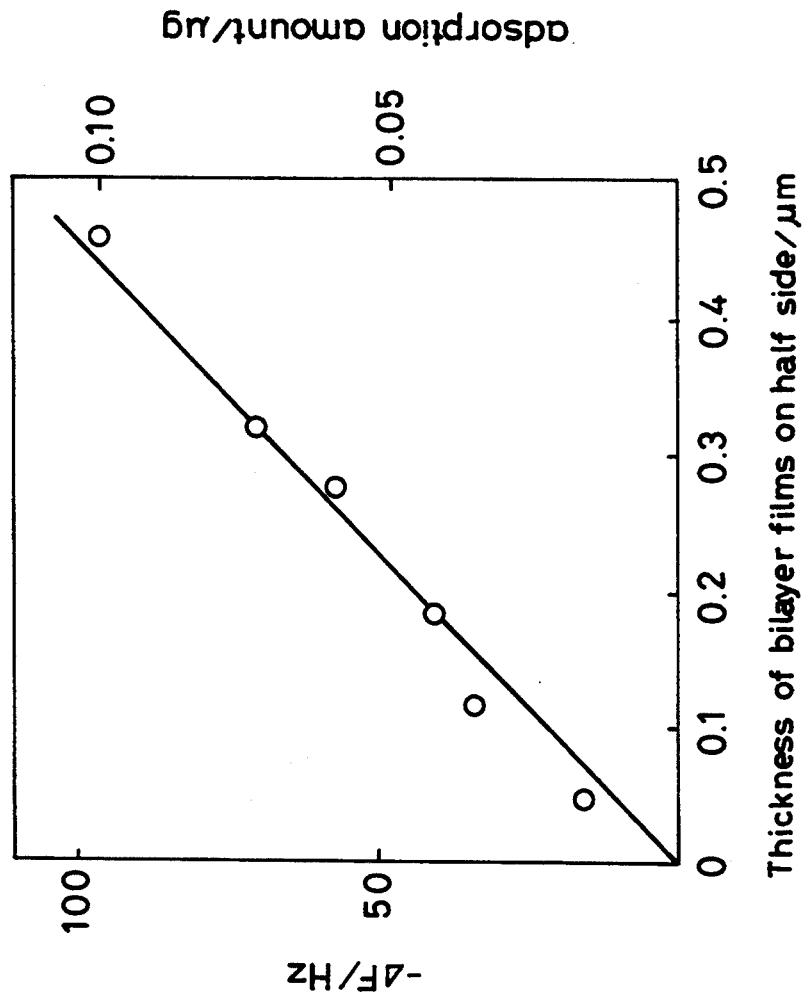
FIG. 19 is a graph showing correlation of adsorption amount and frequency change to thickness of bilayer films.

Adsorption experiments are carried out in the same manner as in Example 2 at 45° C. with varied film thickness of the $2C_{18}N^{+}2C_1/PSS^{-}$ cast film by use of halothane as the anesthetic at a concentration of $3.00\times10^{-4}(M)$. The results are shown in FIG. 19. FIG. 19 shows that the adsorbed amount of halothane is increased with increased film thickness, and that halothane penetrates into the film to be adsorbed.

EXAMPLE 15

Figure 20:
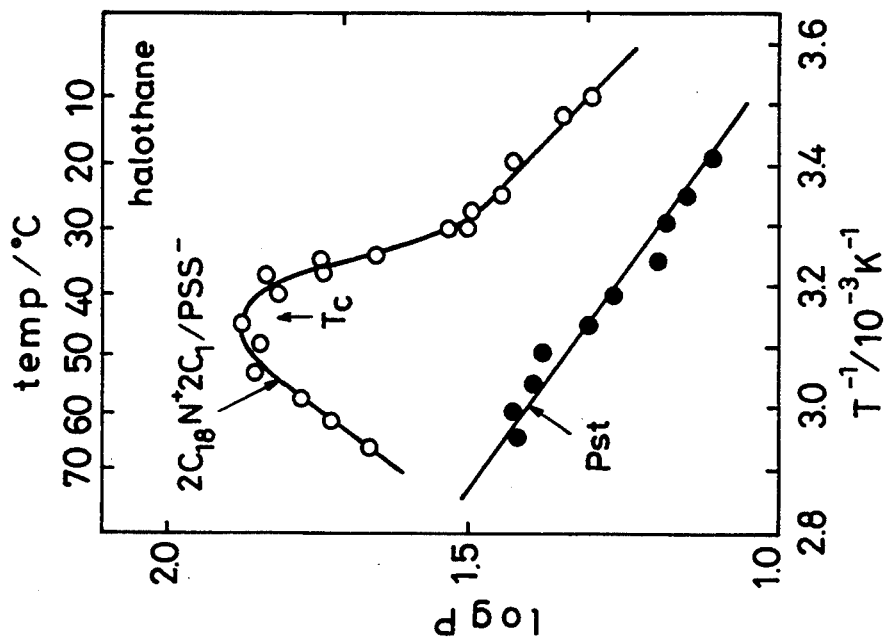
FIG. 20 is a graph showing correlation between temperature and partition coefficient.

Adsorption experiments are carried out in the same manner as in Example 2 at varied temperatures by use of halothane as the anesthetic at a concentration of $9.5\times10^{-4}(M)$ in the aqueous solution. The results are shown in FIG. 20 in the form of an Arrhenius plot. FIG. 20 shows that the partition coefficient of halothane onto the coated film has a maximum at the phase transition temperature (Tc) of the $2C_{18}N^{+}2C_1/PSS^{-}$ cast film, i.e. in the state of liquid crystals.

Figure 21:
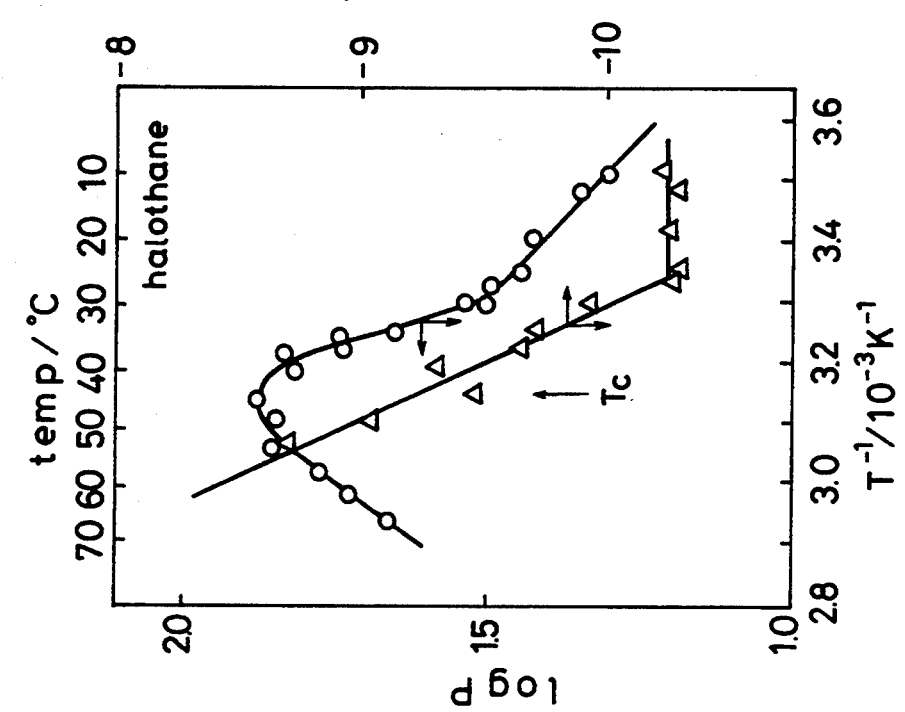
FIG. 21 is a graph showing correlation of partition coefficient and diffusion coefficient to temperature.

An Arrhenius plot of the diffusion coefficient D obtained is shown in FIG. 21. FIG. 21 shows that the diffusion coefficient D of the $2C_{18}N^{+}2C_1/PSS^{-}$ film critically changes near a temperature at which the phase transition from crystals to liquid crystals starts to take place, and it is considered that the diffusion therein is increased in the state of liquid crystals.

Comparative Example 10

The same adsorption experiments as in Example 15 are carried out except for using a polystyrene film in place of the $2C_{18}N^{+}2C_1/PSS^{-}$ film. The results are shown in FIG. 20, resulting in showing quite a different adsorption behavior from the case where the $2C_{18}N^{+}2C_1/PSS^{-}$ film is used.

EXAMPLES 16-18

Comparative Examples 11-16

Adsorption experiments are carried out in the same manner as in Example 2 in gas phase by use of various cast films as shown in Table 5 and by using 2 μg of halothane according to the inject process under the conditions of a film weight of 20 μg and a temperature of 25° C. The results are shown in Table 5. Table 5 shows that the partition coefficients in the gas phase correspond fairly well to those in the aqueous phase as shown in Table 4.

TABLE 5

| | Coated films | Partition Coefficients (P) |
|---|---|---|
| | Polyion complex film | |
| Example 16 | $2C_{18}N^+2C_1/PSS^-$ | 117 |
| Example 17 | Cholesterylammonium poly(p-styrenesulfonate) | 12.7 |
| Example 18 | $CTAB^+/PSS^-$ | 79.6 |
| | Hydrophobic polymer | |
| Comparative Example 11 | Polystyrene [Pst] | 16.9 |
| Comparative Example 12 | Polyvinylchloride [PVC] | 10.2 |
| | Hydrophilic polymer | |
| Comparative Example 13 | Polyvinyl alcohol [PVA] | 0 |
| | Polyamino acid | |
| Comparative Example 14 | Poly($\gamma$-methyl-L-glutamate) [PMLG] | 19.4 |
| | Membrane protein | |
| Comparative Example 15 | Bacteriorhodopsin | 0 |
| Comparative Example 16 | Luciferase | 0 |

EXAMPLE 19

Figure 22:
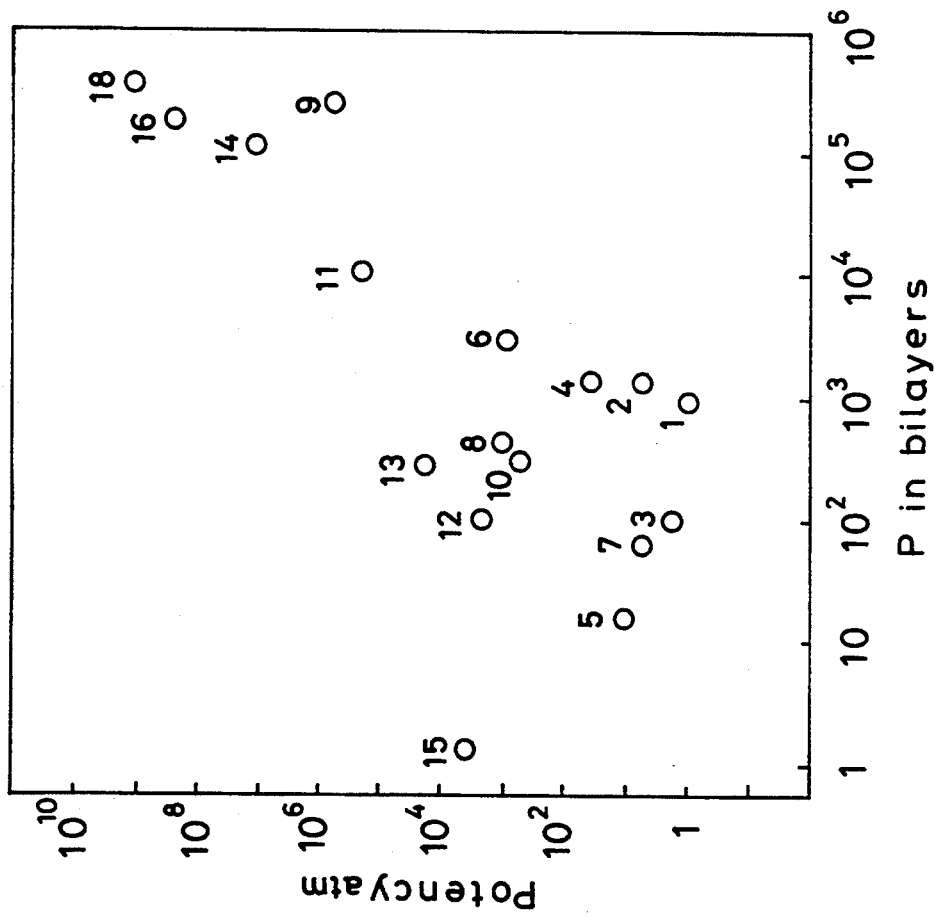
FIG. 22 is a graph showing correlation between partition coefficient and potency.

Adsorption experiments are carried out in the gas phase at 25° C. by use of the same $2C_{18}N^+2C_1/PSS^-$ cast film as in Example 2 for 18 anesthetics shown in Table 6. The results are shown in FIG. 22. In Table 6, "potency" means a value determined by a concentration ratio of the aqueous solution of anesthetics in the aqueous system taking that of methanol as 1.00, whereas "potency (atm)" means a value obtained by converting "potency" to be used in the gaseous system by determining the partial pressure of the anesthetic in the gas phase from the concentration in the aqueous solution thereof followed by determining the partial pressure ratio taking that of methanol as 1.00. FIG. 22 shows a fair correlation between potency (atm) and partition coefficient P, although not so good as in the aqueous system of Example 12.

The above results mean that the anesthetics must be taken into the living body in the aqueous phase in order to be used in real time in the clinical cases, whereas in the gas phase, the detection of the anesthetics provided in the gas phase is satisfactory, resulting in being used all the time, and, if necessary, the potency of the anesthetic may roughly but simply be determined from the partition coefficient in the gas phase system. The above results further mean that a concentration of an anesthetic compound having a known partition coefficient in the gas phase may be determined from the adsorbed amount by use of the bilayer film coated crystal oscillator, useful when an accurate concentration of the anesthetic in the gas phase is required in biological experiments, and in applications to further developments of the anesthetics.

TABLE 6

| No. | Anesthetic compounds | Potency | Potency atm |
|---|---|---|---|
| 1 | methanol | 1.00 | 1.00 |
| 2 | ethanol | 2.43 | 5.19 |
| 3 | acetone | 3.47 | 1.76 |
| 4 | 1-propanol | 9.43 | $4.42 \times 10$ |
| 5 | butanone | $1.20 \times 10$ | $1.51 \times 10$ |
| 6 | diethyl ether | $2.99 \times 10$ | 6.43 |
| 7 | 1-butanol | $4.43 \times 10$ | $9.41 \times 10^2$ |
| 8 | paraldehyde | $5.44 \times 10$ | $8.20 \times 10^2$ |
| 9 | benzyl alcohol | $5.01 \times 10\ 2$ | $6.25 \times 10^5$ |
| 10 | chloroform | $7.62 \times 10\ 2$ | $4.62 \times 10^2$ |
| 11 | 1-hexanol | $1.12 \times 10\ 3$ | $2.23 \times 10^5$ |
| 12 | halothane | $4.47 \times 10\ 3$ | $1.72 \times 10^3$ |
| 13 | methoxyflurane | $4.86 \times 10\ 3$ | $1.82 \times 10^4$ |
| 14 | 1-octanol | $7.93 \times 10\ 3$ | $1.21 \times 10^7$ |
| 15 | pentane | $1.51 \times 10\ 4$ | $3.34 \times 10^3$ |
| 16 | 1-nonanol | $4.03 \times 10\ 4$ | $2.51 \times 10^8$ |
| 17 | hexane | $6.75 \times 10\ 4$ | $5.21 \times 10^4$ |
| 18 | 1-decanol | $1.00 \times 10\ 5$ | $1.11 \times 10^9$ |

EXAMPLE 20

Figure 23:
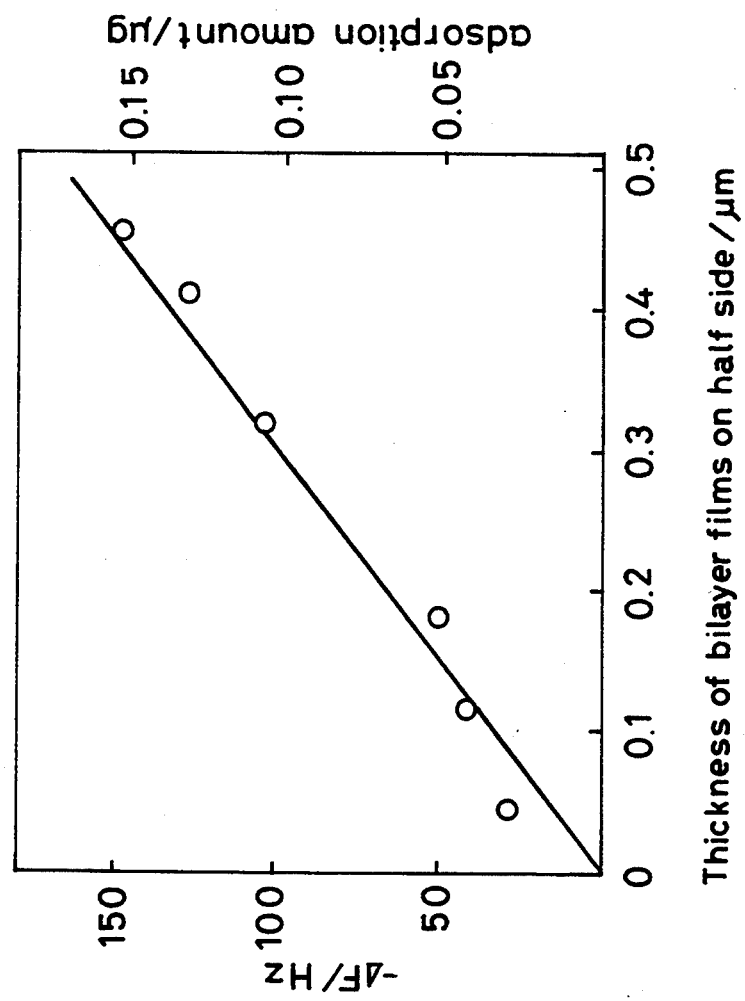
FIG. 23 is a graph showing correlation of adsorption amount and frequency change to thickness of bilayer films.

Adsorption experiments are carried out in the gas phase at 25° C. by use of the same $2C_{18}N^+2C_1/PSS^-$ cast film as in Example 2 and of 2 $\mu$l of halothane as the anesthetic varying the film thickness. The results are shown in FIG. 23. FIG. 23 shows that as the film thickness is increased, the adsorption amount is linearly increased, and this shows that halothane penetrates into the cast film.

EXAMPLE 21

Figure 24:
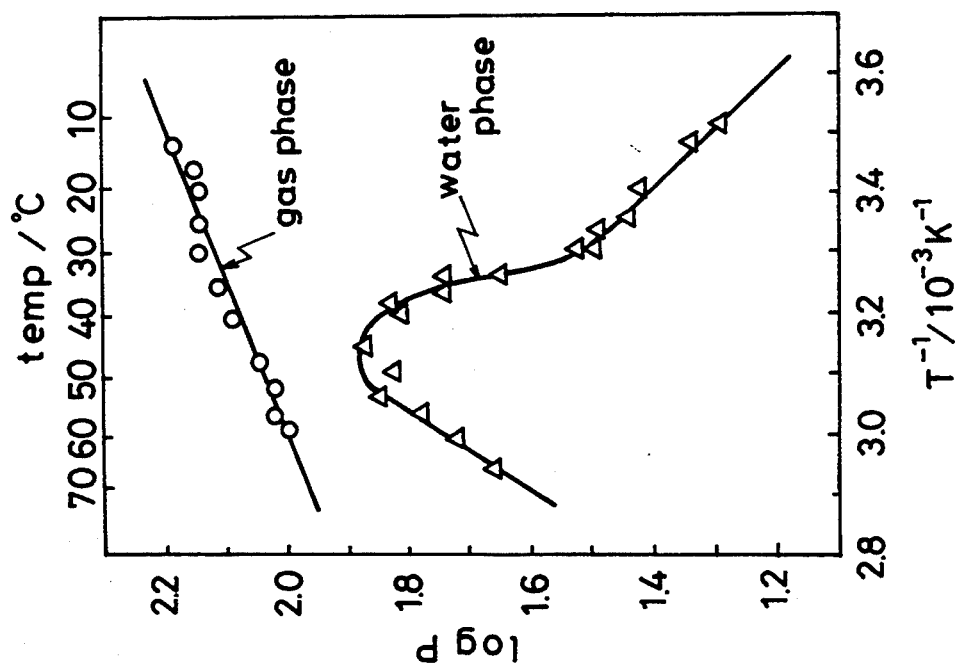

Adsorption experiments are carried out in the gas phase by use of the same $2C_{18}N^+2C_1/PSS^-$ cast film as in Example 2 and of 2 $\mu$l of halothane as the anesthetic at varied temperatures. The results are shown in FIG. 24 along with the results in the aqueous system of Example 15 in the form of an Arrhenius plot. FIG. 24 shows that no phase transition effect is observed in the gas phase differently from that in the aqueous system.

EXAMPLE 22

Figure 25:
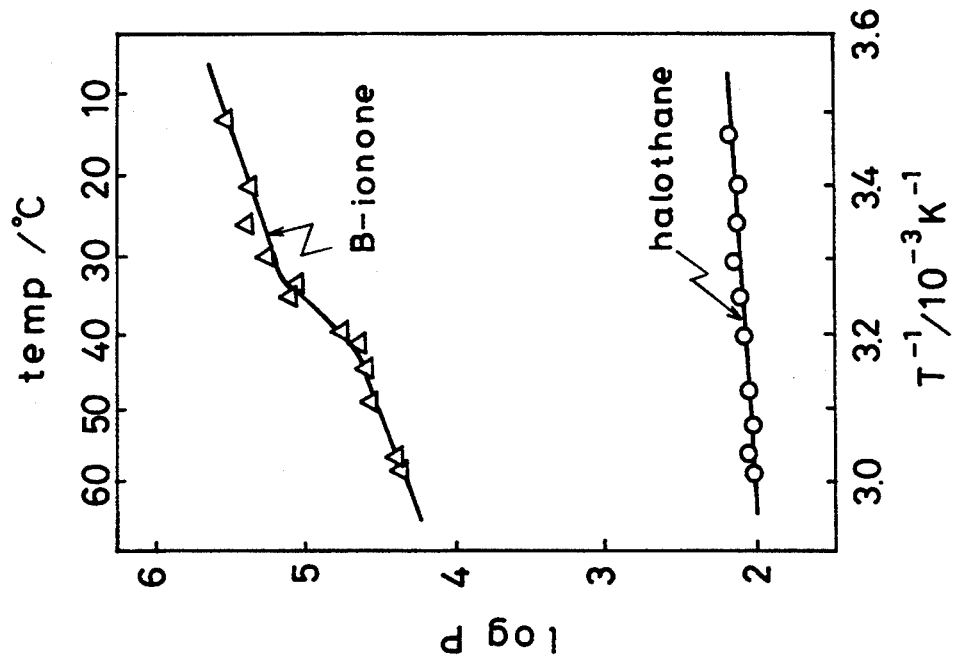
FIG. 24 and FIG. 25 are graphs showing correlation between temperature and partition coefficient respectively.

The same adsorption experiments as in Example 21 are repeated except for using $\beta$-ionone as the odorous substance in place of halothane as the anesthetic. The results are shown in FIG. 25 along with the results of halothane. FIG. 25 shows that a discontinuous Arrhenius plot is observed near the phase transition temperature Tc.

EXAMPLES 23–27

Adsorption experiments are carried out by use of the same crystal oscillator or piezoelectric crystal as in Example 2 and of the bitter or odorous substances shown in Table 7 for five different immobilized bilayer films shown in Table 7. The results are shown in Table 7 in terms of partition coefficient as in Example 4. The results in Table 7 shows that adsorbed amounts of respective components of a mixture of bitter and/or odorous substances may be separately and selectively determined in real time by use of a plurality of detecting apparatuses having different types of immobilized bilayer films respectively.

What is claimed is:

1. A method of detecting bitter substances or odorous substances comprising:
   (a) forming an immobilized bilayer film on a substrate;
   (b) positioning the immobilized bilayer film between a salt containing inner aqueous phase and a salt-containing outer aqueous phase;
   (c) inserting two measuring probes of a galvanostat into the inner and outer aqueous phases, respectively;

(d) injecting a bitter or odorous substance at varied concentrations into the outer aqueous phase, to be adsorbed onto the immobilized bilayer film;

(e) measuring at least one of the respective membrane potentials and membrane resistance of the bilayer film and obtaining a relationship between changes in at least one of the membrane potential or membrane resistance, and the concentrations of the bitter or odorous substance as a curve; and (f) determining an amount of a bitter substance or odorous substance contained in the outer aqueous phase from the change in at least one of the membrane potential or membrane resistance by the application of the above relationship;

wherein the immobilized bilayer is such that the threshold concentrations causing membrane potential changes for bitter substances linearly correspond to biological gustatory threshold values respectively with substantially the same sensitivity as that of the latter, and the threshold concentrations causing membrane potential changes for odorous substances linearly correspond to membrane potential-producing biological olfactory threshold values with substantially the same sensitivity, wherein the biological gustatory threshold value is the minimum amount of the bitter substance needed to trigger a response to the sense of taste, and the biological olfactory threshold value is the minimum amount of the odorous substance needed to trigger a response to the sense of smell; and wherein the immobilized bilayer film is selected from the group consisting of (i) films prepared by blending at least one lipid selected from a synthetic lipid and a natural lipid, with a polymer, followed by casting; (ii) films prepared by impregnating pores of filters having a microporous structure, with a chloroform solution of at least one lipid selected from synthetic lipids and natural lipids, followed by drying; (iii) films obtained by dissolving a polyion complex powder prepared by mixing an aqueous dispersion of at least one lipid selected from synthetic lipids having a cationic hydrophilic group and natural lipids having a cationic hydrophilic group, with an aqueous solution of an anionic polymer, in chloroform, followed by casting; (iv) films obtained by dissolving a polyion complex powder prepared by mixing an aqueous dispersion of at least one lipid selected from synthetic lipids having an anionic hydrophilic group and natural lipids having an anionic hydrophilic group, with an aqueous solution of a cationic polymer, in chloroform, followed by casting; and (v) Langmuir-Blodgett multibilayer films prepared by accumulating monolayers of at least one lipid selected from natural lipids and synthetic lipids, including the natural lipids and the synthetic lipids used in the above films (iii) and (iv), onto a substrate using the Langmuir-Blodgett bilayer technique.

2. A method of detecting bitter substances or odorous substances composing:

(a) forming an immobilized bilayer film on a substrate selected from the electrode of a surface acoustic wave device and the electrode of a crystal oscillator;

(b) dipping the immobilized bilayer film into deionized water or placing the immobilized bilayer film in a gas to measure a baseline frequency produced by the vibration of a crystal of the surface acoustic wave device or a crystal of the crystal oscillator;

(c) injecting a bitter substance or an odorous substance into the deionized water or the gas at varied concentrations to be adsorbed onto the immobilized bilayer film, respectively;

(d) measuring the changes in the frequencies and determining a proportional relationship between frequency changes and adsorbed amounts of the bitter substance or odorous substance; and (e) determining a partition coefficient of the bitter substance or odorous substance between the immobilized bilayer film and an aqueous phase or gas phase from the proportional relationship to determine an amount of a bitter substance or an odorous substance contained in a gaseous or aqueous phase;

wherein the immobilized bilayer is such that a linear correlation exists between biological gustatory threshold values and the threshold concentration $(C_{th})$, at which frequency changes due to adsorption of bitter substances are observed respectively, and a linear correlation exists between biological olfactory threshold values and threshold concentrations $(C_{th})$, at which frequency changes due to adsorption of odorous substances are observed respectively, wherein the threshold concentrations $(C_{th})$ are specific for a particular bitter substance or odorous substance, the partition coefficients are specific to a particular bitter substance or odorous substance, the biological gustatory threshold value is the minimum amount of the bitter substance needed to trigger a response to the sense of taste, and the biological olfactory threshold value is the minimum amount of the odorous substance needed to trigger a response to the sense of smell; and wherein the immobilized bilayer film is selected from the group consisting of (i) films prepared by blending at least one lipid selected from a synthetic lipid and a natural lipid, with a polymer, followed by casting; (ii) films prepared by impregnating pores of filters having a microporous structure, with a chloroform solution of at least one lipid selected from synthetic lipids and natural lipids, followed by drying; (iii) films obtained by dissolving a polyion complex powder prepared by mixing an aqueous dispersion of at least one lipid selected from synthetic lipids having a cationic hydrophilic group and natural lipids having a cationic hydrophilic group, with an aqueous solution of an anionic polymer, in chloroform, followed by casting; (iv) films obtained by dissolving a polyion complex powder prepared by mixing an aqueous dispersion of at least one lipid selected from synthetic lipids having an anionic hydrophilic group and natural lipids having an anionic hydrophilic group, with an aqueous solution of a cationic polymer, in chloroform, followed by casting; and (v) Langmuir-Blodgett multibilayer films prepared by accumulating monolayers of at least one lipid selected from natural lipids and synthetic lipids, including the natural lipids and the synthetic lipids used in the above films (iii) and (iv), onto a substrate using the Langmuir-Blodgett bilayer technique.

3. A method as claimed in claim 2, wherein a SAW device is used in place of the crystal oscillator.

4. A method as claimed in claim 1 or 2, wherein the immobilized bilayer film is prepared by a process in which dialkylammonium salt ion and polystyrenesulfonic acid ion are reacted at a raised temperature to form precipitates of polyion complex followed by reprecipitation and drying, and the resulting precipitates are dissolved in chloroform to be cast on the substrate or the electrode of the crystal oscillator.

5. A method as claimed in claim 1 or 2, wherein the bitter substance is selected from a group consisting of strychnine, quinine, nicotine, phenylthiourea, papaverine, caffeine, naringin, and octaacetyl sucrose.

6. A method as claimed in claims 1 or 2, wherein said high molecular weight compounds are selected from polyvinyl chloride, polystyrene, polycarbonate, polyvinyl alcohol and acetyl cellulose.

7. A method as claimed in claims 1 or 2 wherein said filter having a microporous structure is a milliporefilter.

8. A method as claimed in claims 1 or 2, wherein said anionic high polymer is selected from polystyrene sulfonic acid, heparin, polyvinyl-sulfonic acid, polyacrylic acid and polyglutamic acid.

9. A method as claimed in claims 1 and 2, wherein said cationic high polymer is selected from polyallylamine polyethylene imine, and quaternary polyaminostyrene.

10. A method as claimed in claim 1 or 2, wherein the odorous substances is selected from odorants, perfumes, anesthetics and malodorants.

11. A method as claimed in claim 10, wherein the odorous substance is an odorant which is selected from a group consisting of $\beta$-ionone, aliphatic alcohols, campher, amylacetate, vanilline, ethylbutylate, phenol and aldehydes.

12. A method as claimed in claim 10, wherein the odorous substance is a malodorant which is selected from ketones, amines, imines, aldehydes, organic acids, sulfur compounds, styrene, malodor-emitting industrial wastes, foul breath-producing substances, and mixtures thereof.

13. A method as claimed in claim 10, wherein the odorous substance is a perfume which is selected from a group consisting of p-anisaldehyde, 1-undecanol, anisalcohol, anisol, phenylethyl acetate, citral, methyl salicylate, benzyl acetate, tetrahydrogeraniol, terpineol, and geranyl acetate.

14. A method as claimed in claim 13, wherein the immobilized bilayer film is such that a logarithm of partition coefficient (log P) has a linear correlation with perfume intensity.

15. A method as claimed in claim 10, wherein the odorous substance is an anesthetic which is selected from a group consisting of methanol, ethanol, acetone, 1-propanol, butanone, diethyl ether, 1-butanol, paraldehyde, benzylalcohol, chloroform, 1-hexanol, halothane, methoxyflurane, 1-octanol, pentane, 1-nonanol, hexane, and 1-decanol.

16. A method as claimed in claim 15, wherein the immobilized bilayer film is such that concentrations of respective anesthetics have a linear correlation with adsorbed amounts represented by frequency changes to show a constant partition coefficient respectively, that the partition coefficients for respective anesthetics have a linear correlation with the potencies thereof, that the diffusion coefficient D for respective anesthetics has a linear correlation with the potency, and that the threshold value for respective anesthetics has a linear correlation with the potency.

17. An apparatus for use in a method of detecting bitter substances or odorous substances which method comprises:

(a) forming an immobilized bilayer film on a substrate;

(b) positioning the immobilized bilayer film between a salt containing inner aqueous phase and a salt-containing outer aqueous phase;

(c) inserting two measuring probes of a galvanostat into the inner and outer aqueous phases, respectively;

(d) injecting a bitter or odorous substance at varied concentrations into the outer aqueous phase, to be adsorbed onto the immobilized bilayer film, respectively;

(e) measuring at least one of the respective membrane potentials and membrane resistance of the bilayer film and obtaining a relationship between changes in at least one of the membrane potential or membrane resistance, and the concentrations of the bitter or odorous substance as a curve; and (f) determining an amount of a bitter substance or odorous substance contained in the outer aqueous phase from the change in at least one of the membrane potential or membrane resistance by the application of the above relationship;

wherein the immobilized bilayer is such that the threshold concentrations causing membrane potential changes for bitter substances linearly correspond to biological gustatory threshold values respectively with substantially the same sensitivity as that of the latter, and the threshold concentrations causing membrane potential changes for odorous substances linearly correspond to membrane potential-producing biological olfactory threshold values with substantially the same sensitivity, wherein the biological gustatory threshold value is the minimum amount of the bitter substance needed to trigger a response to the sense of taste, and the biological olfactory threshold value is the minimum amount of the odorous substance needed to trigger a response to the sense of smell;

said apparatus comprising:

(1) an inner cell containing a salt-containing inner aqueous solution;

(2) an outer cell containing a salt-containing outer aqueous solution;

(3) an immobilized bilayer film fixed to the inner cell and positioned so as to form a barrier between the inner and outer aqueous solutions; and (4) a galvanostat having measuring probes inserted into the inner and outer aqueous solutions respectively;

wherein the immobilized bilayer film is selected from the group consisting of (i) films prepared by blending at least one lipid selected from a synthetic lipid and a natural lipid, with a polymer, followed by casting; (ii) films prepared by impregnating pores of filters having a microporous structure, with a chloroform solution of at least one lipid selected from synthetic lipids and natural lipids, followed by drying; (iii) films obtained by dissolving a polyion complex powder prepared by mixing an aqueous dispersion of at least one lipid selected from synthetic lipids having a cationic hydrophilic group and natural lipids having a cationic hydrophilic group, with an aqueous solution of an anionic polymer, in chloroform, followed by casting; (iv) films obtained by dissolving a polyion complex powder prepared by mixing an aqueous dispersion of at least one lipid selected from synthetic lipids having an anionic hydrophilic group and natural lipids having an anionic hydrophilic group, with an aqueous solution of a cationic polymer, in chloroform, followed by casting; and (v) Langmuir-Blodgett multibilayer films prepared by accumulating monolayers of at least one lipid selected from natural lipids and synthetic lipids, including the natural lipids and the synthetic lipids used in the above films (iii) and (iv), onto a substrate using the Langmuir-Blodgett bilayer technique.

18. An apparatus for use in a method of detecting bitter substances or odorous substances, said method comprising:

(a) forming an immobilized bilayer film on a substrate selected from the electrode of a surface acoustic wave device and the electrode of a crystal oscillator;

(b) dipping the immobilized bilayer film into deionized water or placing the immobilized bilayer film in a gas to measure a baseline frequency produced by the vibration of a crystal of the surface acoustic wave device or a crystal of the crystal oscillator;

(c) injecting a bitter substance or an odorous substance into the deionized water or the gas at varied concentrations to be adsorbed onto the immobilized bilayer film, respectively;

(d) measuring the changes in the frequencies and determining a proportional relationship between frequency changes and adsorbed amounts of the bitter substance or odorous substance; and (e) determining a partition coefficient of the bitter substance or odorous substance between the immobilized bilayer film and an aqueous phase or a gaseous phase from the proportional relationship to determine an amount of a bitter substance or an odorous substance contained in a gaseous or aqueous phase;

wherein the immobilized bilayer is such that a linear correlation exists between biological gustatory threshold values and the threshold concentration ($C_{th}$), at which frequency changes due to adsorption of bitter substances are observed respectively, and a linear correlation exists between biological olfactory threshold values and threshold concentrations ($C_{th}$), at which frequency changes due to adsorption of odorous substances are observed respectively, wherein the threshold concentrations ($C_{th}$) are specific for a particular bitter substance or odorous substance, the partition coefficients are specific to a particular bitter substance or odorous substance, the biological gustatory threshold value is the minimum amount of the bitter substance needed to trigger a response to the sense of taste, and the biological olfactory threshold value is the minimum amount of the odorous substance needed to trigger a response to the sense of smell;

wherein said apparatus comprises:

(1) a cell containing deionized water, or an aqueous solution of the substance to be measured;

(2) a substrate selected from an electrode of a crystal oscillator or a surface acoustic wave device;

(3) an immobilized bilayer film cast on said substrate, wherein the substrate containing the immobilized bilayer film is submerged in the aqueous solution; and (3) a frequency measuring means connected to the electrode;

wherein the immobilized bilayer film is selected from the group consisting of (i) films prepared by blending at least one lipid selected from a synthetic lipid and a natural lipid, with a polymer, followed by casting; (ii) films prepared by impregnating pores of filters having a microporous structure, with a chloroform solution of at least one lipid selected from synthetic lipids and natural lipids, followed by drying; (iii) films obtained by dissolving a polyion complex powder prepared by mixing an aqueous dispersion of at least one lipid selected from synthetic lipids having a cationic hydrophilic group and natural lipids having a cationic hydrophilic group, with an aqueous solution of an anionic polymer, in chloroform, followed by casting; (iv) films obtained by dissolving a polyion complex powder prepared by mixing an aqueous dispersion of at least one lipid selected from synthetic lipids having an anionic hydrophilic group and natural lipids having an anionic hydrophilic group, with an aqueous solution of a cationic polymer, in chloroform, followed by casting; and (v) Langmuir-Blodgett multibilayer films prepared by accumulating monolayers of at least one lipid selected from natural lipids and synthetic lipids, including the natural lipids and the synthetic lipids used in the above films (iii) and (iv), onto a substrate using the Langmuir-Blodgett bilayer technique.

19. An apparatus as claimed in claim 18, wherein said substrate is the electrode of a SAW device.

20. An apparatus as claimed in claims 17 or 18, wherein said high molecular weight compounds are selected from polyvinyl chloride, polystyrene, polycarbonate, polyvinyl alcohol and acetyl cellulose.

21. An apparatus as claimed in claims 17 or 18 wherein said filter having a microporous structure is a milliporefilter.

22. An apparatus as claimed in claims 17 or 18, wherein said anionic high polymer is selected from polystyrene sulfonic acid, heparin, polyvinyl-sulfonic acid, polyacrylic acid and polyglutamic acid.

23. An apparatus as claimed in claims 17 and 18, wherein said cationic high polymer is selected from polyallylamine, polyethylene imine, and quaternary polyaminostyrene.

24. A method as claimed in claim 1 or 2, wherein the synthetic lipid is selected from a group consisting of ammonium salts, sulfonates, carboxylates in the form of trialkyl, dialkyl and/or monoalkyl a represented by the formula:

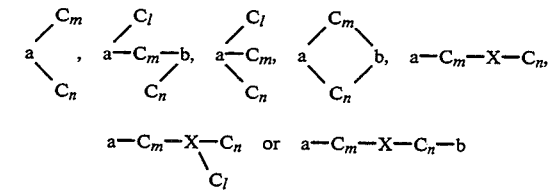

where a and b represent a hydrophilic group moiety selected from $-N^+(CH_3)_3$, $-SO_3^-$, $PO_4^-$, polyol, and polyether, $C_l$, $C_m$ and $C_n$ represent a hydrophobic group moiety selected from alkyl group, fluoroalkyl group, and alkylene group having a $C_8$, or higher carbon chain, and X represents a rigid segment selected from diphenylazomethylene group, biphenyl group, naphthalene group, and anthracene group.

25. A method as claimed in claims 1, 2, 17 or 18 wherein the natural lipid is selected from a group consisting of phosphatidyl chlorine and phosphatidyl serine.

* * * * *